US012728070B2

(12) United States Patent
Lurie et al.

(10) Patent No.: US 12,728,070 B2
(45) Date of Patent: Sep. 8, 2026

(54) HEAD UP CPR DEVICE WITH INTEGRATED VENTILATOR

(71) Applicant: Keith G. Lurie, Minneapolis, MN (US)

(72) Inventors: Keith G. Lurie, Minneapolis, MN (US); Anja Metzger, Lake Elmo, MN (US); Philip Tetzlaff, Minneapolis, MN (US); Wayne Seibrecht, Golden, CO (US)

(73) Assignee: Resuscitation Innovations LLC, Minneapolis, MN (US)

( * ) Notice: Subject to any disclaimer, the term of this patent is extended or adjusted under 35 U.S.C. 154(b) by 1096 days.

(21) Appl. No.: 17/668,266

(22) Filed: Feb. 9, 2022

(65) Prior Publication Data

US 2022/0265508 A1 Aug. 25, 2022

Related U.S. Application Data

(63) Continuation-in-part of application No. 16/201,339, filed on Nov. 27, 2018, now abandoned.

(60) Provisional application No. 63/148,055, filed on Feb. 10, 2021, provisional application No. 62/599,465, filed on Dec. 15, 2017, provisional application No. 62/591,029, filed on Nov. 27, 2017.

(51) Int. Cl.

| | |
|---|---|
| ***A61H 31/00*** | (2006.01) |
| ***A61M 16/06*** | (2006.01) |
| ***A61M 16/20*** | (2006.01) |

(52) U.S. Cl.

CPC ......... *A61H 31/005* (2013.01); *A61H 31/006* (2013.01); *A61H 31/007* (2013.01); *A61M 16/06* (2013.01); *A61M 16/208* (2013.01)

(58) Field of Classification Search

CPC .. A61H 31/004; A61H 31/005; A61H 31/006; A61H 31/007; A61H 31/008; A61H 2201/1623; A61H 2201/1207; A61H 2201/5058; A61H 2201/1409; A61H 2230/30; A61M 16/06; A61M 16/208; A61M 16/0066; A61M 16/0084; A61M 16/022; A61M 16/024; A61M 2209/08

See application file for complete search history.

(56) References Cited

U.S. PATENT DOCUMENTS

| | | | |
|---|---|---|---|
| 3,965,893 | A | 6/1976 | Ragailler |
| 3,985,126 | A | 10/1976 | Barkalow |

(Continued)

FOREIGN PATENT DOCUMENTS

| | | | |
|---|---|---|---|
| DE | 102021120926 A1 * | 2/2023 | ........ A61M 16/0003 |

OTHER PUBLICATIONS

Allison, 2023, Chest compression rates of 60/min versus 90/min during neonatal cardiopulmonary resuscitation: a randomized controlled animal trial, frontiers in pediatrics, p. 1 (Year: 2023).*

(Continued)

*Primary Examiner* — Brandy S Lee

(74) *Attorney, Agent, or Firm* — Kilpatrick Townsend & Stockton LLP

(57) ABSTRACT

A head up CPR system may include a base and an upper support coupled with the base and configured to elevate a patient's upper body. The system may include a chest compression device that is coupleable with one or both of the base and the upper support and a positive pressure ventilation system that is coupleable with the base.

19 Claims, 24 Drawing Sheets

(56) References Cited

U.S. PATENT DOCUMENTS 4,060,079 A 11/1977 Reinhold, Jr.
4,198,963 A * 4/1980 Barkalow ......... A61M 16/0409 128/207.15
4,702,231 A * 10/1987 Arpin ..................... A61H 31/00 601/106
5,454,773 A 10/1995 Blanchard et al.
5,454,779 A 10/1995 Lurie et al.
5,551,420 A 9/1996 Lurie et al.
5,645,522 A 7/1997 Lurie et al.
5,692,498 A 12/1997 Lurie et al.
5,730,122 A 3/1998 Lurie
6,029,667 A 2/2000 Lurie
6,062,219 A 5/2000 Lurie et al.
6,155,257 A 12/2000 Lurie et al.
6,224,562 B1 5/2001 Lurie et al.
6,234,985 B1 5/2001 Lurie et al.
6,526,973 B1 3/2003 Lurie et al.
6,604,523 B2 8/2003 Lurie et al.
6,986,349 B2 1/2006 Lurie
7,056,296 B2 6/2006 Herman et al.
7,060,041 B1 6/2006 Weil et al.
7,082,945 B2 8/2006 Lurie
7,195,012 B2 3/2007 Lurie
7,195,013 B2 3/2007 Lurie
7,204,251 B2 4/2007 Lurie
7,410,649 B2 8/2008 Yoshimi et al.
7,569,021 B2 8/2009 Sebelius et al.
7,766,011 B2 8/2010 Lurie
7,836,881 B2 11/2010 Lurie
7,938,115 B2 5/2011 Thompson et al.
9,707,152 B2 7/2017 Lurie et al.
9,801,782 B2 10/2017 Lurie et al.
10,137,265 B2 11/2018 Freeman et al.
11,103,672 B1 8/2021 Lurie et al.
2002/0069878 A1 6/2002 Lurie et al.
2002/0177793 A1* 11/2002 Sherman .............. A61H 31/006 601/41
2003/0004445 A1* 1/2003 Hall ..................... A61H 31/006 601/44
2004/0162510 A1* 8/2004 Jayne ................... A61H 31/005 601/44
2004/0162587 A1* 8/2004 Hampton ........... A61N 1/39044 601/44
2006/0089574 A1* 4/2006 Paradis ................ A61H 31/005 601/41
2008/0255482 A1 10/2008 Lurie
2010/0031961 A1 2/2010 Schmidt
2010/0319691 A1* 12/2010 Lurie .................... A61M 16/04 128/205.24
2011/0201979 A1 8/2011 Voss et al.
2012/0016179 A1* 1/2012 Paradis ................ A61N 1/3987 601/41
2012/0203147 A1* 8/2012 Lurie ................... A61K 31/522 514/250
2012/0222677 A1* 9/2012 Lee ................... A61M 16/0078 128/205.14
2012/0330199 A1 12/2012 Lurie et al.
2012/0330200 A1 12/2012 Voss et al.
2013/0281897 A1 10/2013 Hoffman et al.
2014/0135668 A1 5/2014 Belalcazar
2015/0231026 A1 8/2015 Lurie
2015/0231027 A1 8/2015 Lurie
2015/0231028 A1 8/2015 Belalcazar
2015/0328417 A1 11/2015 Loser et al.
2016/0058660 A1 3/2016 Lurie et al.
2016/0128899 A1* 5/2016 Lurie ................. A61G 13/1215 601/41
2016/0228326 A1 8/2016 Lurie et al.
2016/0317385 A1 11/2016 Salcido et al.
2016/0338904 A1 11/2016 Lurie et al.
2017/0119622 A1 5/2017 Lurie et al.
2017/0258677 A1 9/2017 Lurie et al.
2017/0368280 A1 12/2017 Dermel et al.
2018/0133103 A1 5/2018 Lurie
2018/0147378 A1 5/2018 Jacquot et al.
2018/0154094 A1 6/2018 Jacquot et al.
2018/0261128 A1* 9/2018 Tan .................... A61N 1/39044
2019/0008720 A1 1/2019 Joshi et al.
2019/0021943 A1* 1/2019 Nilsson ................ A61H 31/005
2019/0117506 A1* 4/2019 Falk ....................... A61H 1/006
2019/0159963 A1 5/2019 Lurie
2019/0167931 A1* 6/2019 Kantor ................... A61B 5/349
2019/0269574 A1* 9/2019 Lurie ................... A61H 31/004
2021/0020068 A1 1/2021 Tan et al.

OTHER PUBLICATIONS

Final Office Action issued in U.S. Appl. No. 16/201,339, dated Aug. 30, 2021 in 24 pages.

Non-Final Office Action issued in U.S. Appl. No. 16/201,339, dated Feb. 26, 2021 in 30 pages.

Aufderheide TP, et al. Death by Hyperventilation: A Common and Life-Threatening Problem During Cardiopulmonary Resuscitation, Crit Care Med. Sep. 2004;32(9 Suppl):S345-51.

Lurie KG, et al. Optimizing Standard Cardiopulmonary Resuscitation with an Inspiratory Impedance Threshold Valve. Chest. Apr. 1998;113(4):1084-90.

* cited by examiner 100
104
106
108
150
102
132

Carrying Case (Backpack)
Airway compartment: ITD, SGA, facemask
Defibrillation compartment: AED and manual ACD CPR device
Main compartment: SAVE CPR System
200
500
504
506
508
509
510
512
514
516

FIG. 9
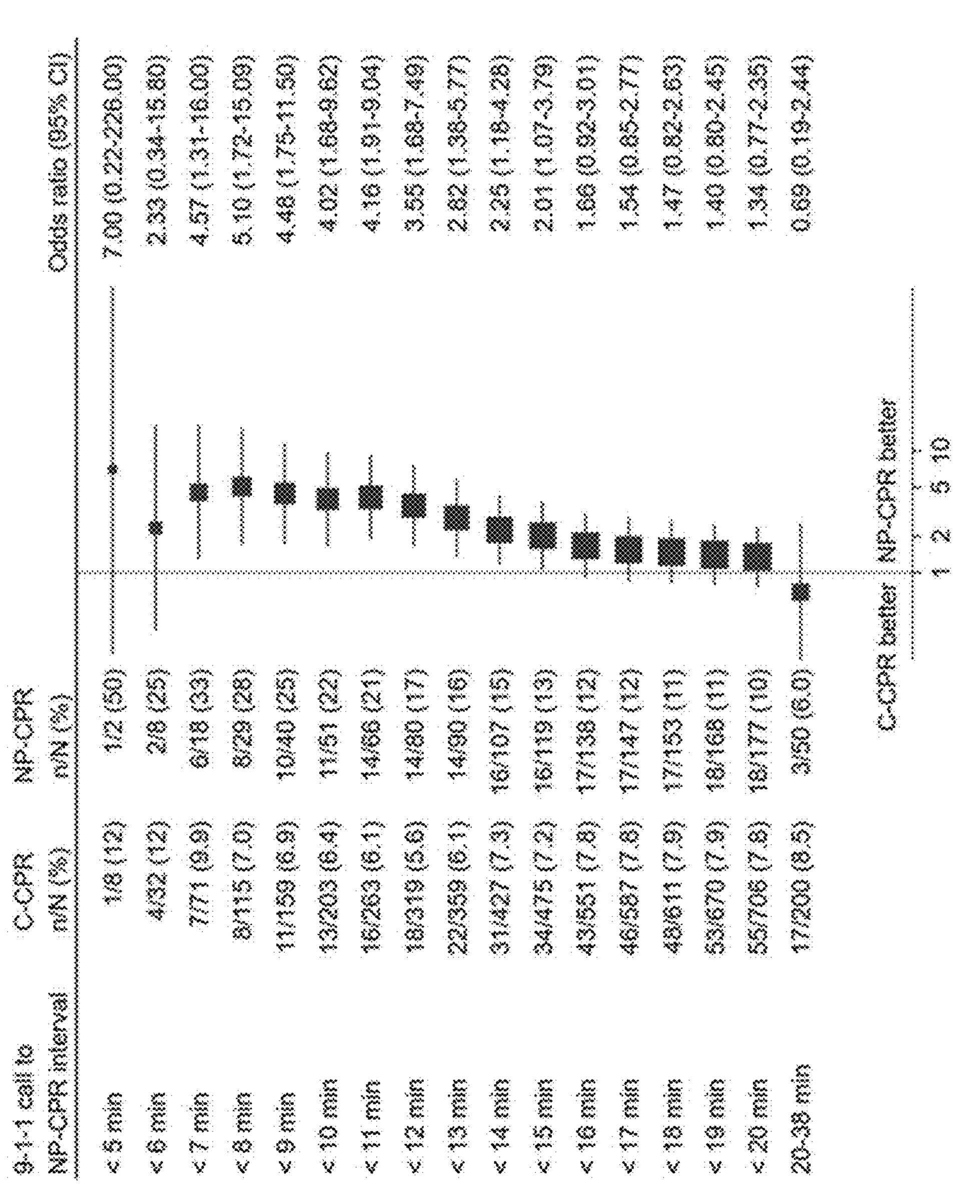

FIG. 10
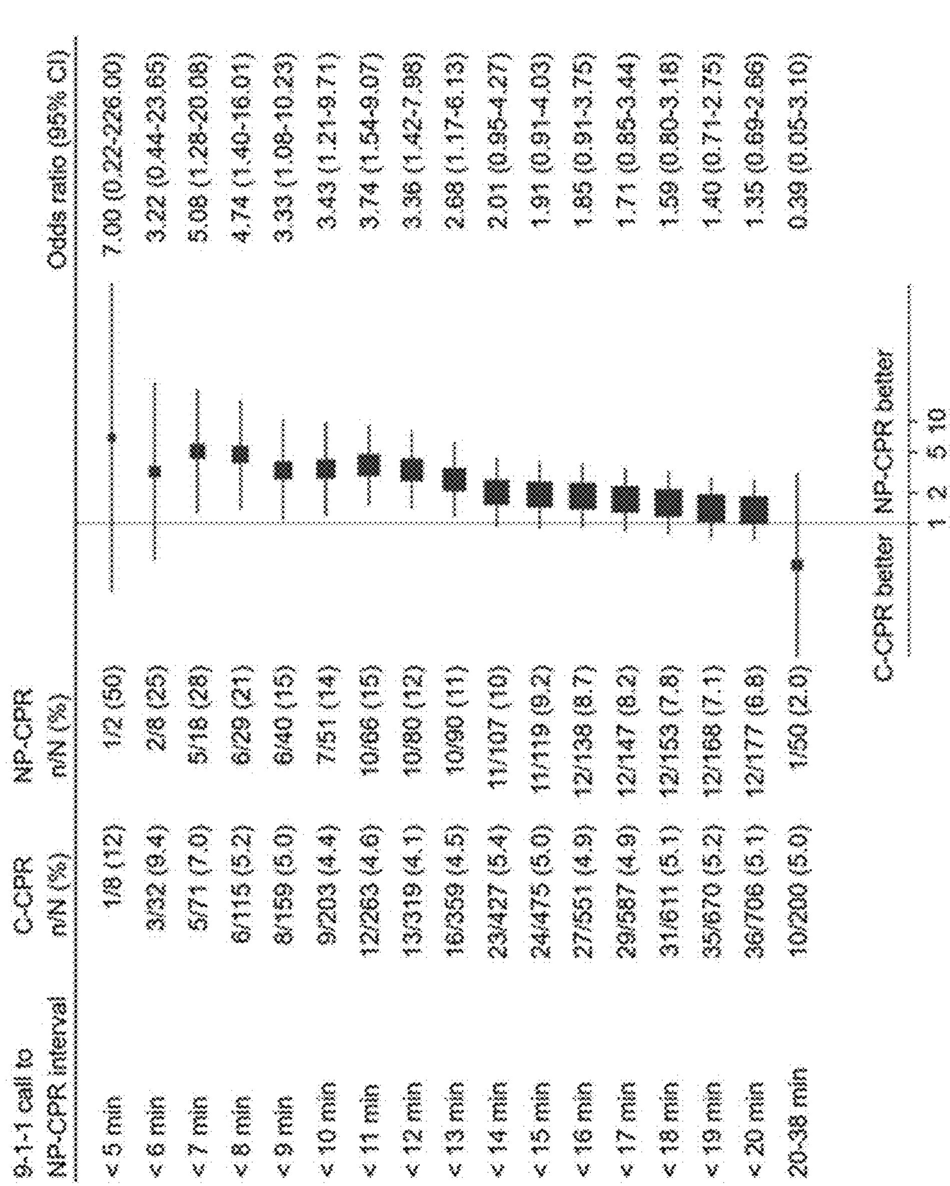

HEAD UP CPR DEVICE WITH INTEGRATED VENTILATOR

CROSS-REFERENCE TO RELATED APPLICATIONS

This application claims priority to U.S. Provisional Patent Application No. 63/148,055, filed Feb. 10, 2021, the disclosure of which is incorporated by reference herein in its entirety.

BRIEF SUMMARY OF THE INVENTION

This application is also a continuation-in-part of U.S. Nonprovisional patent application Ser. No. 16/201,339, filed Nov. 27, 2018, which claims priority to U.S. Provisional Patent Application No. 62/599,465, filed Dec. 15, 2017, and also claims priority to U.S. Provisional Application No. 62/591,029, filed Nov. 27, 2017, the disclosures of which are incorporated by reference herein in their entireties.

Embodiments of the present invention may encompass head up CPR systems. The systems may include a base. The systems may include an upper support coupled with the base and configured to elevate a patient's upper body. The systems may include a chest compression device that is coupleable with one or both of the base and the upper support. The systems may include a positive pressure ventilation system that is coupleable with one or both of the base and the upper support.

In some embodiments, the positive pressure ventilation system may include a manual resuscitator bag. The positive pressure ventilation system may include a mechanical linkage system. The positive pressure ventilation system may include an actuator that drives the mechanical linkage system. The systems may include an impedance threshold device that is configured to be interfaced with the positive pressure ventilation system. The systems may include an automated external defibrillator. The systems may include a carrying case that includes at least one compartment that is configured to receive one or more of the base, the upper support, the chest compression device, and the positive pressure ventilation system. The carrying case may include a plurality of shoulder straps. The chest compression device may be further configured to actively decompress an individual's chest between each compression. The positive pressure ventilation system may be configured to receive a signal that synchronizes delivery of a positive pressure ventilation with one or more phases of CPR compression/decompression cycles with one or both of continuous uninterrupted chest compressions and interrupted chest compressions. The positive pressure ventilation system may be controlled by one or both of an on/off switch and a signal that synchronizes delivery of a positive pressure ventilation with a phase of CPR. The one or more phases of CPR may be decompression phases. The signal may be received from one or both of a sensor and a controller. The systems may include a sensor to detect a timing of a compression/decompression cycle of the chest compression device and to provide the signal that synchronizes delivery of a positive pressure ventilation with a phase of CPR. The positive pressure ventilation system may be configured to deliver positive pressure ventilations that have durations of between about 300 msec and 1200 msec. The positive pressure ventilation system may include a resuscitator bag and an automated resuscitator bag compressor. The resuscitator bag may be removable from the automated resuscitator bag compressor for operation in a manual mode. The positive pressure ventilation system, the upper support, and the chest compression device may be controlled by a same controller system. The upper support may be configured to elevate the a patient's upper body from a starting position to an elevated position over a period of between about 30 seconds and 10 minutes. The systems may include a controller that is configured to adjust one or more of a ventilation rate, a tidal volume, and a compression:ventilation ratio. The positive pressure ventilation system may include at least one actuator selected from the group consisting a resuscitator bag squeezer, a blower-type ventilator, a turbine based ventilator, and a piston based ventilator. The positive pressure ventilation system may include at least one ventilator selected from the group consisting of a volume-controlled ventilator, a pressure controlled ventilator, and a combined pressure/volume controlled ventilator. The positive pressure ventilation system may be configured to receive a selection for one or more parameters selected from the group consisting of a positive pressure ventilation delivery rate, a tidal volume, and a duration of positive pressure ventilation delivery. The selection may be based at least in part on measurements from one or more physiological sensors.

Some embodiments of the present technology may encompass methods of resuscitating a sudden cardiac arrest patient. The methods may include positioning a patient on a head up CPR system such that a chest compression device of the head up CPR system is aligned with the patient's heart. The methods may include elevating a portion of the patient's upper body. The methods may include performing chest compressions and active chest decompressions on the patient using a chest compression device of the head up CPR system while the portion of the patient's upper body is elevated. The methods may include delivering positive pressure ventilations using a positive pressure ventilation device of the head up CPR system.

In some embodiments, delivery of the positive pressure ventilations may be synchronized with a phase of CPR. The phase of CPR may be a decompression phase. The methods may include actively decompressing the patient's chest between each chest compression. The methods may include regulating an intrathoracic pressure of the patient while the portion of the patient's upper body is elevated. The positive pressure ventilations may be delivered while the portion of the patient's upper body is elevated. Elevating a portion of the patient's upper body may include elevating the patient's head from a first height of between about 8-10 cm to a second height of between about 15-25 cm. Elevating a portion of the patient's upper body may include elevating the patient's head from the first height to the second height over a period of between about 20 and 240 seconds. Elevating a portion of the patient's upper body may include elevating the patient's head from the first height to the second height over a period of between about 90 and 120 seconds.

Some embodiments of the present technology may encompass methods of resuscitating a sudden cardiac arrest patient that may include performing chest compressions on the patient using an active compression-decompression CPR device that is coupled with a positive pressure breath delivery system that is synchronized with a phase of a CPR cycle using a sensor to provide periodic controlled positive pressure ventilation and improve cerebral perfusion pressure.

In some embodiments, the phase of the CPR cycle may include a decompression phase. The active compression-decompression CPR device may be coupled with the positive pressure breath delivery system mechanically, through a sensor, or both mechanically and through a sensor. The methods may include improving a cerebral perfusion pressure of the patient. A chest compression rate may be slowed from around 90-120 compressions/min to 50-80 compressions per minute to allow for more time during the decompression phase when a positive pressure breath is delivered and synchronized with the decompression phase of the CPR cycle.

Some embodiments of the present technology may encompass positive pressure ventilation systems. The systems may include a resuscitator bag. The systems may include an automated bag compressor configured to alternately compress the resuscitator bag to deliver positive pressure ventilations. The systems may include a communications interface configured to receive a signal indicating a timing of a phase of CPR. The systems may include a controller that is configured to synchronize operation of the automated bag compressor to deliver positive pressure ventilations during all or part of a selected phase of CPR. In some embodiments, the selected phase of CPR may include a decompression phase.

Some embodiments of the present technology may encompass positive pressure ventilation systems that may include a positive pressure ventilation device. The systems may include a communications interface configured to receive a signal indicating a timing of a phase of CPR. The systems may include a controller that is configured to synchronize operation of the automated bag compressor to deliver positive pressure ventilations during all or part of a selected phase of CPR. In some embodiments, the selected phase of CPR may include a decompression phase.

Some embodiments of the present technology may encompass methods of delivering a positive pressure ventilations. The methods may include sensing a compression/decompression cycle of CPR. The methods may include setting a timing of positive pressure ventilations based on the compression/decompression cycle. The methods may include delivering positive pressure ventilations based on the timing.

In some embodiments, setting a timing of positive pressure ventilations may be further based on a measurement of one or more physiological parameters. The one or more physiological parameters may include an end tidal $CO_2$ measurement.

BRIEF DESCRIPTION OF THE DRAWINGS

A further understanding of the nature and advantages of various embodiments may be realized by reference to the following figures. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

FIG. 1C depicts a locking handle of the head up CPR system of FIG. 1A.

FIG. 9 is a graph illustrating a comparison of survival to hospital discharge between conventional (C) and neuroprotective (NP) CPR according to time interval from the 9-1-1-emergency call for help to Automated Head Up Position device placement after propensity-score matching.

FIG. 10 is a graph illustrating a comparison of survival to hospital discharge with favorable neurological outcome between conventional (C) and neuroprotective (NP) CPR according to time interval from the 9-1-1-emergency call for help to Automated Head Up Position device placement after propensity-score matching.

DETAILED DESCRIPTION OF THE INVENTION

Figure 1A:
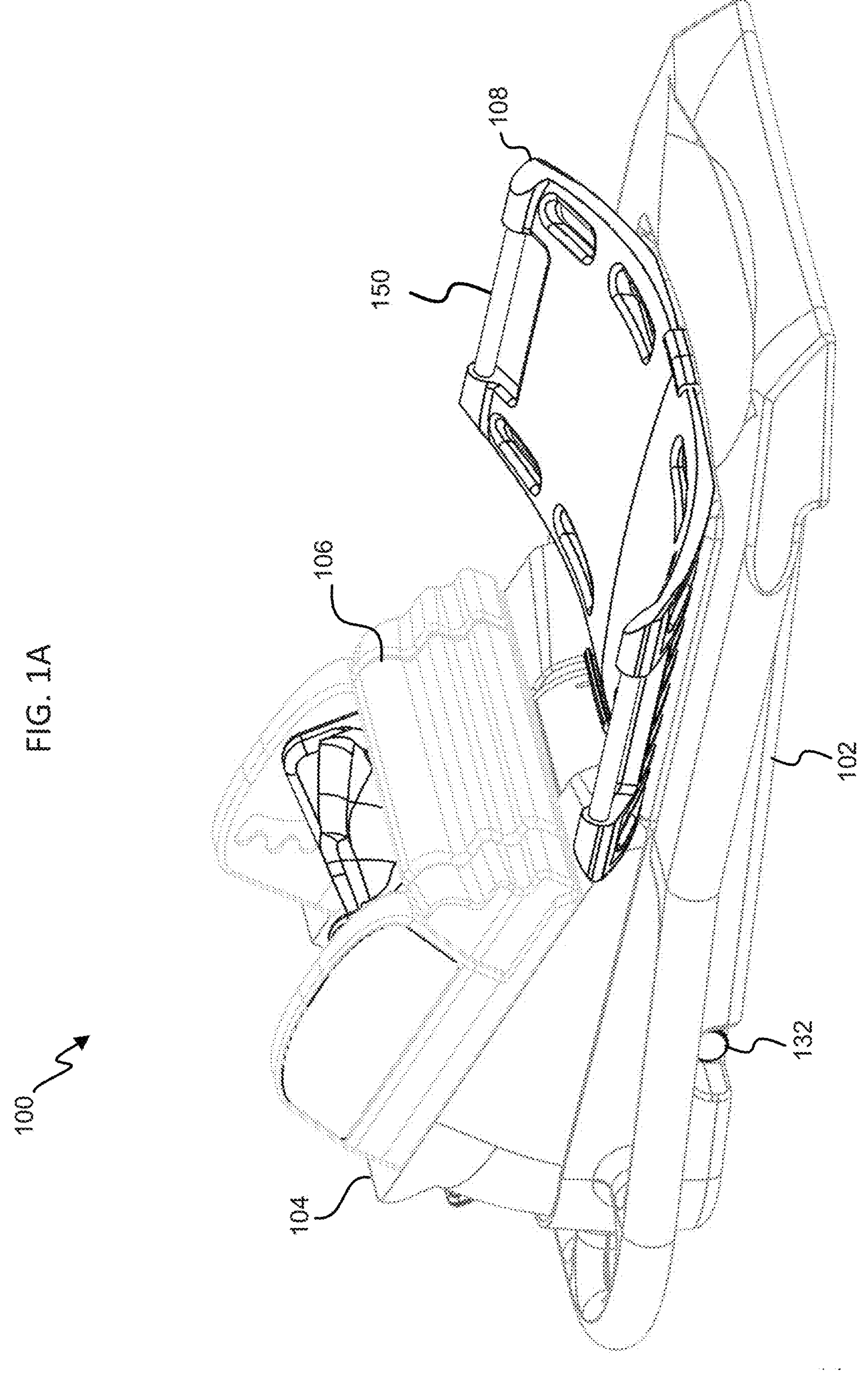
FIG. 1A depicts a head up CPR system in a lowered position according to embodiments.

Embodiments of the present invention are directed to comprehensive ACD+ITD Head Up (HUP) CPR systems. HUP CPR, in combination with an ITD and ACD CPR, provides a unique means to harness gravity to protect the brain from ischemic, anoxic, and concussive injuries during and after CPR. Conventional CPR (C-CPR) in the flat position has been the standard of care since 1960 when C-CPR was first described. However, C-CPR without circulatory adjuncts (e.g., ACD+ITD CPR) is unable to deliver sufficient blood flow to the brain, with C-CPR over time providing cerebral perfusion pressures that are at <10% of pre-cardiac arrest values. In contrast, HUP CPR with circulatory adjuncts, such as ACD+ITD CPR or an ITD alone, can be used to nearly normalize cerebral perfusion pressure (CerPP). HUP CPR requires these circulatory adjuncts to pump blood 'uphill' to the brain. The increase in brain blood flow with HUP CPR, together with a reduction in intracranial pressure (ICP), helps preserve brain function and significantly improve survival rates of patients suffering sudden cardiac arrest.

The HUP CPR systems described herein may enable basic life support providers (e.g., a fire crew without paramedics) to rapidly deliver fully automated CPR, including automated synchronized mechanical positive pressure ventilation (mPPV), to increase the likelihood of neurologically intact survival after sudden cardiac arrest. By using automated ACD CPR devices in conjunction with controlled sequential elevation of the head and thorax and automated synchronized positive pressure ventilation, embodiments of the present invention may reduce or eliminate problems associated with hyperventilation of the patient due to excessive PPV rates and/or incomplete chest wall recoil during the decompression phase of CPR. Such systems may also increase crew safety by reducing the risk of airborne disease transmission by fully automating the delivery of positive pressure ventilations during CPR. Embodiments may utilize head up systems that elevate the head and thorax in a controlled manner to optimize brain perfusion during performance of CPR on a patient that is experiencing sudden cardiac arrest. In some embodiments, the head up systems may be used in combination with ACD CPR and/or an impedance threshold device (ITD) and/or other intrathoracic pressure regulation device. The combination of HUP CPR combined with ACD CPR and an ITD uniquely harnesses gravity to enhance drainage of venous blood from the head and neck, lower intracranial pressure (ICP), and markedly increase systemic and cerebral blood flow and likelihood for survival. By incorporating the various components (HUP device, ACD CPR device, ITD, ventilator, etc.) into a single device, the head up CPR systems of the present invention may enable medical personnel to deploy necessary treatment more rapidly, which may lead to higher survival rates.

Turning now to FIGS. 1A-1M, one embodiment of a Head Up (HUP) CPR system 100 is illustrated. HUP CPR system 100 may include a base 102 that supports and is pivotally or otherwise operably coupled with an upper support 104. Upper support 104 may include a neck pad or neck support 106, as well as areas configured to receive a patient's upper back, shoulders, neck, and/or head. An elevation mechanism may be configured to adjust the height and/or angle of the upper support 104 throughout the entire ranges of 0° and 45° relative to the horizontal plane and between about 5 cm and 45 cm above the horizontal plane. In some embodiments, the upper support 104 may be configured to elevate the middle of the patient's head to a height that is between about 2 and 42 cm above a middle of the heart. In some embodiments, an angle between the middle of the patient's head and a middle of the heart is between about 10 and 40 degrees relative to horizontal.

A user may be positioned on the HUP CPR system 100 with his neck positioned on the neck support 106. In some embodiments, the neck support 106 may contact the individual's spine at a location near the C7 and C8 vertebrae. This position may help maintain the individual in the sniffing position, to help enable optimum ventilation of the individual. In some embodiments, the individual may be aligned on the HUP CPR system 100 by positioning his nipples just above a center line of a back plate 108. In some embodiments, the back plate 108 may be removably coupled with the base 102 and/or upper support 106. In some embodiments, the back plate 108 may have a contoured upper surface. The back plate 108 may include coupling 150 that may be used to mount a chest compression device (not shown) to the HUP CPR system 100. For example, the chest compression device may be coupled with the back plate 108 using the coupling 150 such that the chest compression device is in alignment with the individual's sternum at a generally orthogonal angle to ensure that the chest compressions are delivered at a proper angle and with proper force. In some embodiments, the alignment of the chest compression device may be achieved by configuring the chest compression device to pivot and/or otherwise adjust angularly to align the chest compression device at an angle substantially orthogonal to the sternum.

Figure 1B:
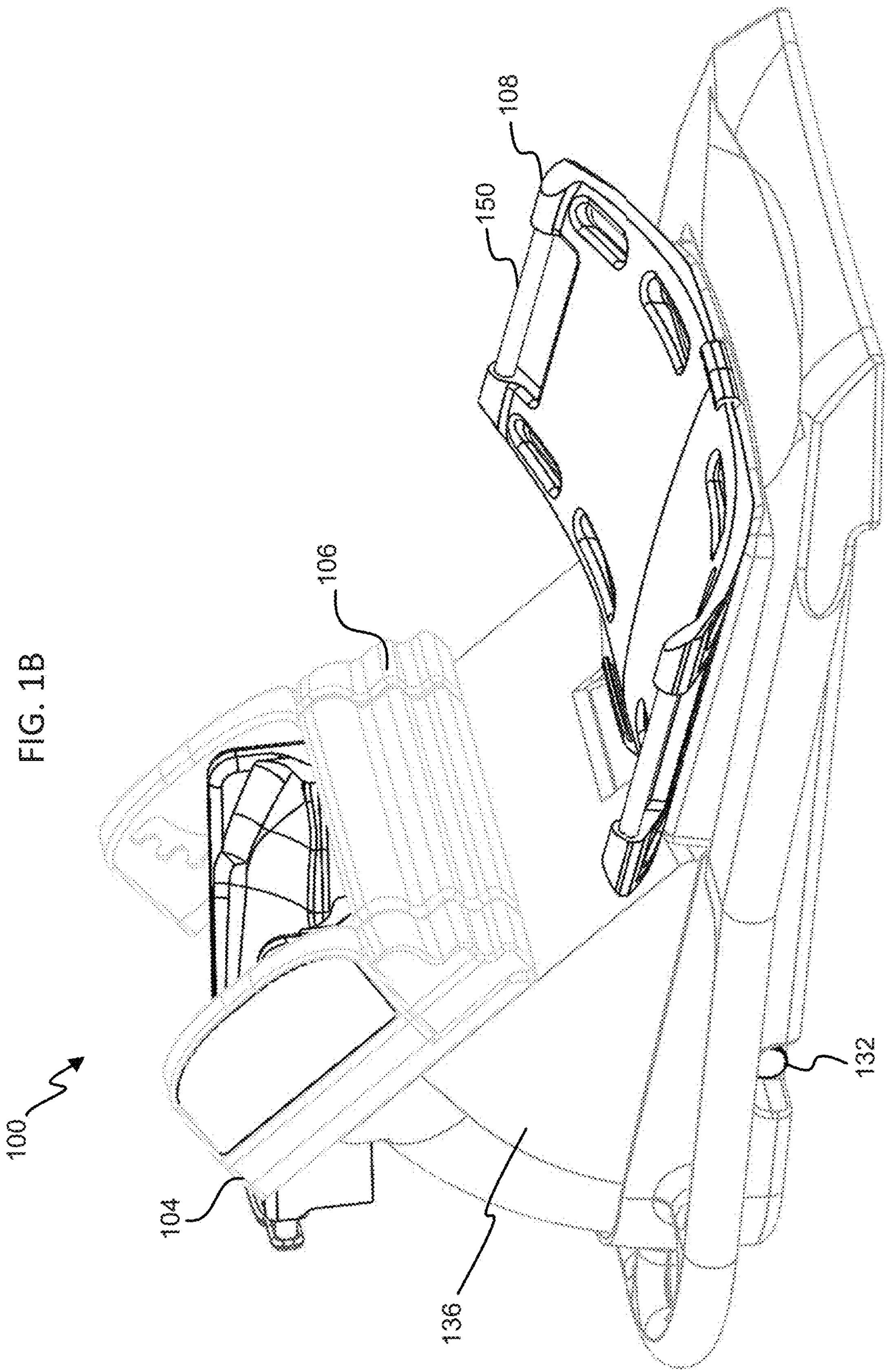
FIG. 1B depicts the head up CPR system of FIG. 1A in an elevated position.
Figure 1C:
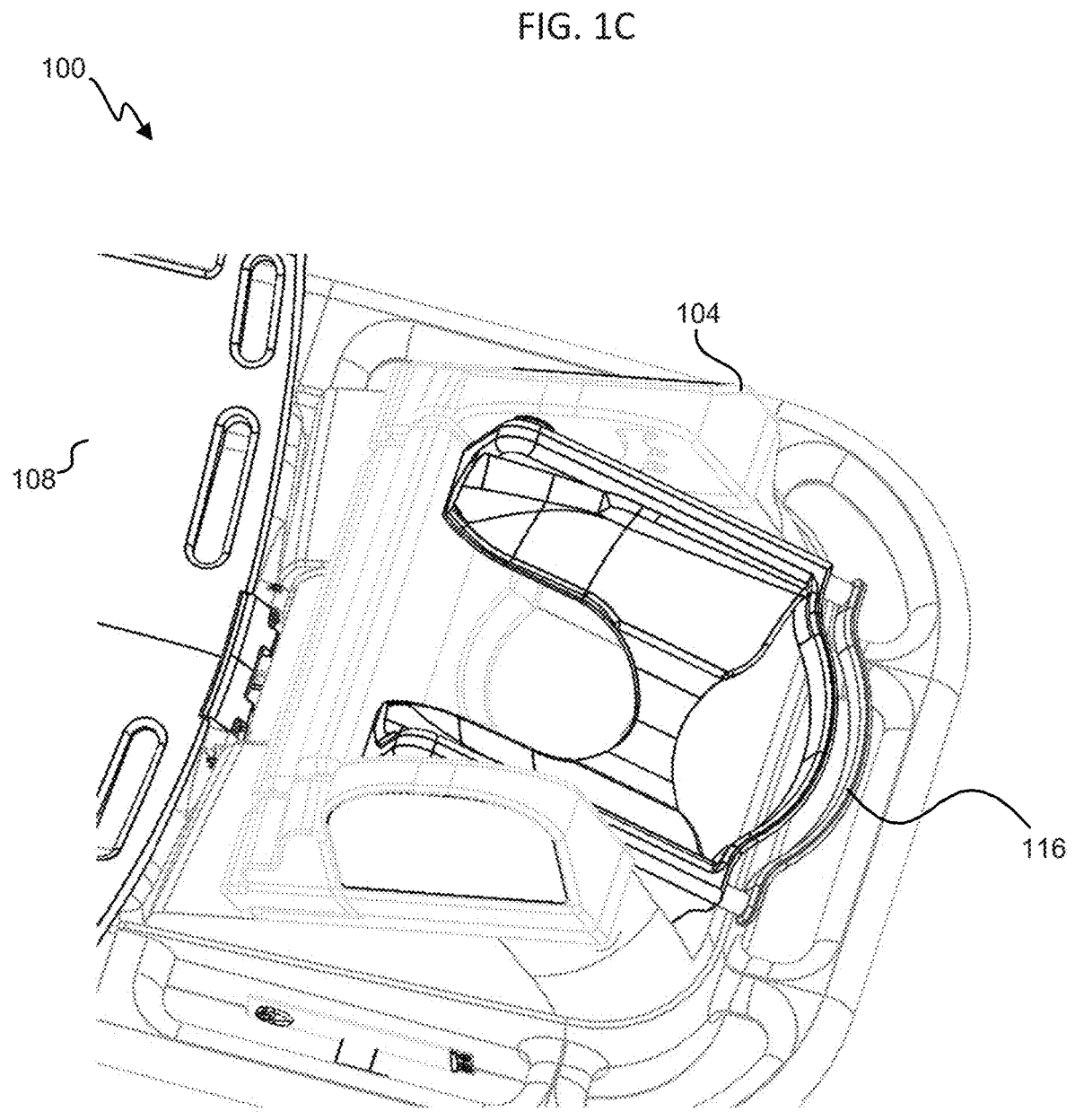
Figure 1D:
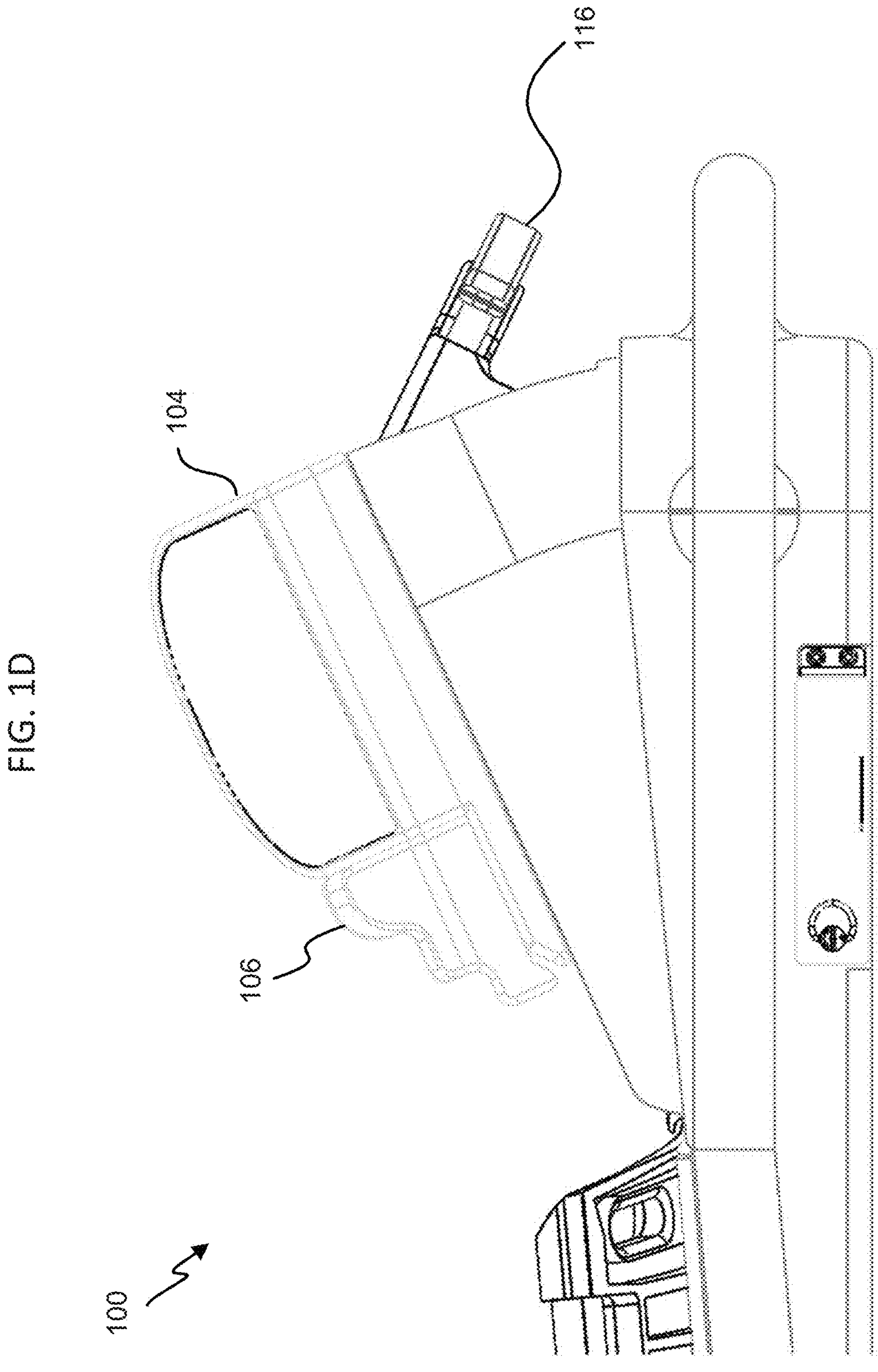
FIG. 1D depicts the locking handle of the head up CPR system of FIG. 1A.

When in a lowered position, as shown in FIG. 1A, the upper support 104 may maintain the patient's head at a position that is slightly elevated relative to the heart, which is supported by back plate 108. In the lowered position, a head-receiving portion of the upper support 104 (which is designed to maintain the patient in the sniffing position and extends downward from a top surface of the upper support 104) maintains the base of the head at a generally horizontal level (within about 5 degrees) when in a fully lowered position. The upper support 104 may be raised to elevate the patient's head, shoulders, and/or heart between the lowered position and a fully elevated position (and any position therebetween), as shown in FIG. 1B. For example, the upper support 104 may be maneuvered to support the head at heights of between about 5 cm and 45 cm relative to a horizontal support surface on which the base 102 is supported. Upper support 104 may be configured to be adjustable such that the upper support 104 may slide along a longitudinal axis of base 102 to accommodate patients of different sizes as well as to accommodate movement of a patient associated with the elevation of the head by upper support 104. Without such sliding ability, a patient's upper body has a tendency to curl forward on the HUP CPR system 100 as the patient's upper body is elevated. The upper support 104, including neck support 106, may be extended away from the back plate 108 when the upper support 104 is elevated. In some embodiments, this sliding movement may be locked once an individual is positioned on the elevated upper support 104. In some embodiments, the upper support 104 may include one or more springs that may bias the upper support 104 toward the torso. This allows the upper support 104 to slide in a controlled manner when the individual's body shifts during the elevation process. In some embodiments, the one or more springs may have a total spring force of between about 5 lb. and about 50 lbs., more commonly between about 15 lb. and about 30 lb. Such force allows the upper support 104 to maintain a proper position, yet can provide some give as the head and upper torso are elevated. Further, the elevation device may include a slide mechanism such that with elevation of the head and neck the portion of elevation device behind the head and shoulder elongates. For example, the slide mechanism may include roller bearings that are mounted on a track that allows the upper support 104 to slide to accommodate patients of different sizes as well as to handle shifting of the body during elevation, which helps to maintain the neck in the sniffing position. In some embodiments, such as those shown in FIGS. 1C and 1D, a locking handle 116 is provided that allows medical personnel to adjust a lateral position of the upper support 104 relative to the base 102. To actuate the handle 124, a user must apply force to push a distal portion 126 of the handle 124 toward a fixed, proximal portion 128 of the handle 116. This action pushes a locking member (not shown) into a free space of a ratchet mechanism, allowing the user to adjust the lateral position of the upper support 104. Once released, the locking member may enter a tooth of the ratchet to set a position of the upper support 104 based on a size of the user. The upper support 104 may then only slide in small amounts to handle the shifting of the patient throughout the elevation process.

Figure 1E:
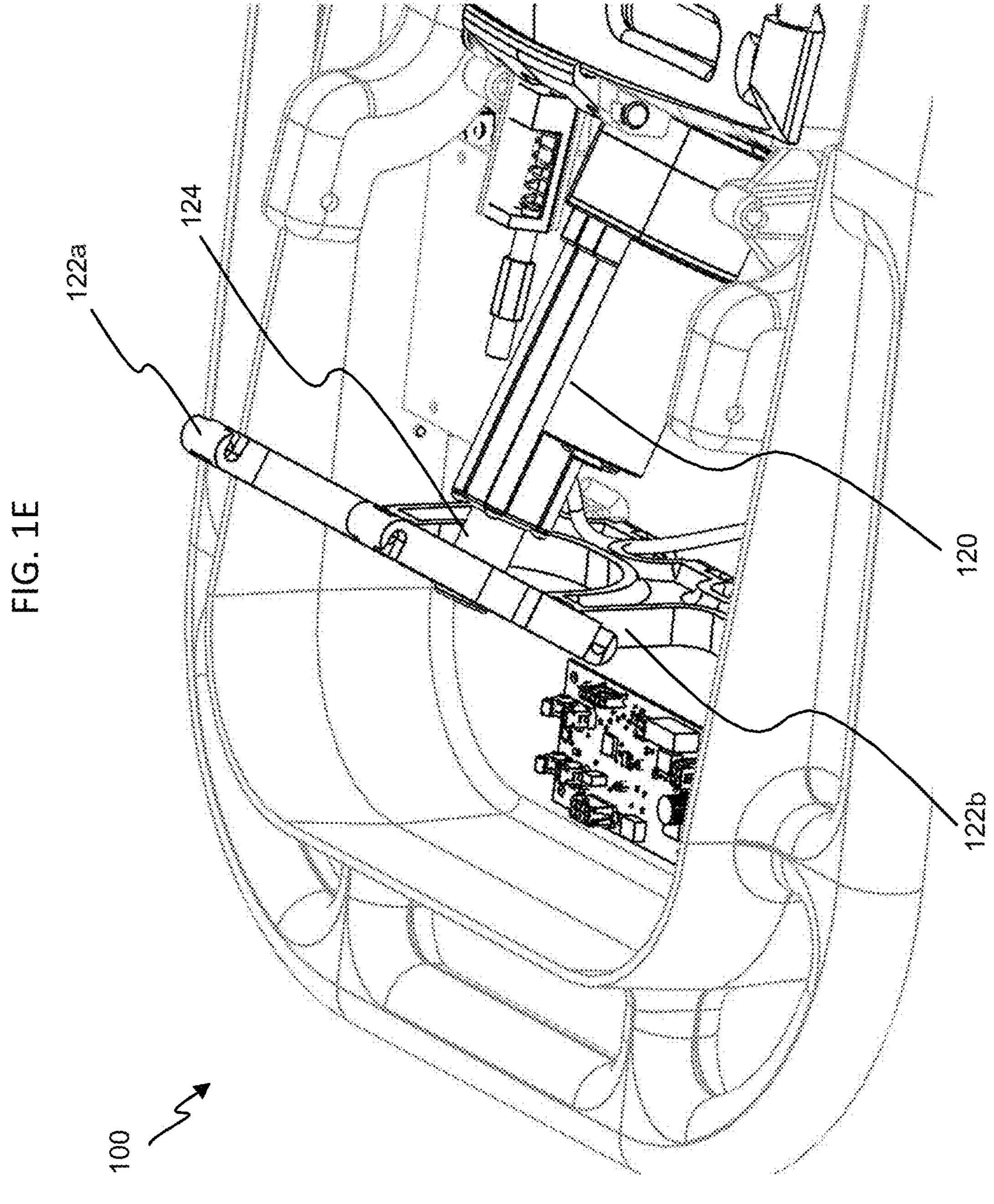
FIG. 1E depict a linear actuator of the head up CPR system of FIG. 1A in an elevated position.
Figure 1F:
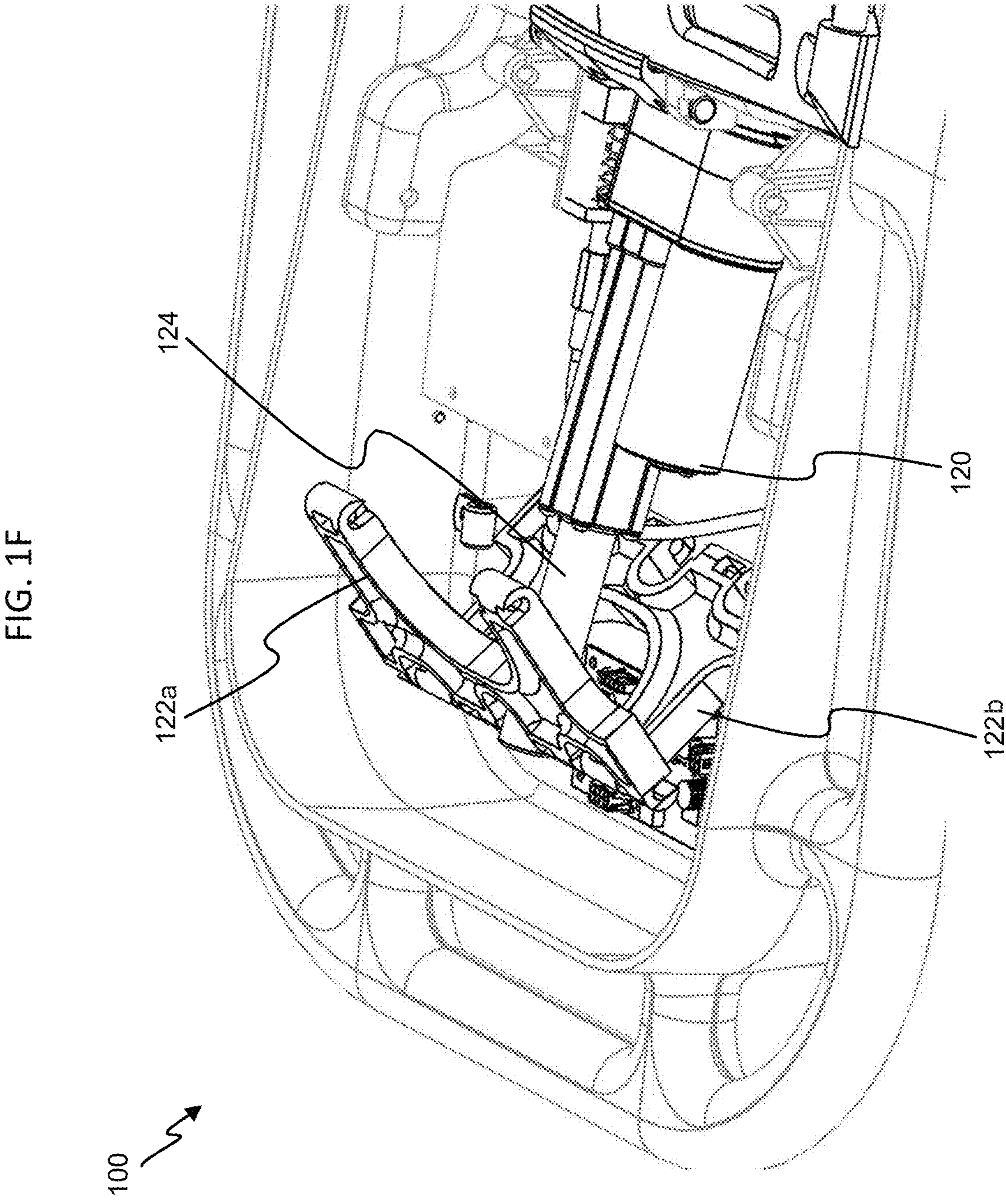
FIG. 1F depict the linear actuator of the head up CPR system of FIG. 1A in a lowered position.

FIGS. 1E and 1F depict a linear actuator 120 that is used to raise and lower the upper support 104. Linear actuator 120 is coupled at a joint formed between two or more support members 122. Support members 122 are coupled between the base 102 and a bottom surface of the upper support 104 such that top support member(s) 122*a* is coupled with the upper support 104 and the bottom support member(s) 122*b* is coupled with the base 102. As linear actuator 120 is operated, a rod 124 of the linear actuator 120 shortens to draw the joint of the support members 122 toward the back plate 108, which causes an angled between the top and bottom support members 122 to increase, such as shown in FIG. 1E, forcing the upper support 104 upward to elevate a patient's upper body. When operated in reverse, the rod 124 of linear actuator 120 extends, pushing on the joint to decrease the angle between the top and bottom support members 122 as shown in FIG. 1F, thereby lowering the upper support 104. It will be appreciated that the direction of operation of the linear actuator 120 and support members 122 may be reversed in some embodiments such that lengthening rod 124 causes elevation of the upper support 104 and shortening of rod 124 causes the lowering of the upper support 104. While shown here with a linear actuator 120 and support member 122 elevation mechanism, it will be appreciated that HUP CPR system 100 may additionally or alternatively include other elevation mechanisms, such as threaded rods, lead screws, pneumatic and/or hydraulic actuators, motor driven telescopic rods, other elevation mechanisms, and/or combinations thereof.

Turning back to FIGS. 1A and 1B, the back plate 108 may be sized and shaped to receive a portion of the patient's back, just behind the heart and may be configured to couple with a chest compression device (not shown). Examples of CPR assist devices that could be used with the elevation device (either in the current state or a modified state) include the LUCAS device, sold by Physio-Control, Inc. and described in U.S. Pat. No. 7,569,021, the entire contents of which is hereby incorporated by reference, the Defibtech Lifeline ARM—Hands-Free CPR Device, sold by Defibtech, the Thumper mechanical CPR device, sold by Michigan Instruments, automated CPR devices by Zoll, such as the AutoPulse, as also described in U.S. Pat. No. 7,056,296, the entire contents of which is hereby incorporated by reference, the Weil Mini Chest Compressor Device, such as described in U.S. Pat. No. 7,060,041 (Weil Institute), and the like. Chest compression devices used in accordance with the present invention may be configured to compress and/or actively decompress the chest.

In some embodiments, the back plate 108 may have a curved profile that may provide some flexibility to the back plate 108. This flexibility helps when the HUP CPR system 100 is used in conjunction with a chest compression device, as the flexibility ensures that the right amount force applied to the patient's chest. For example, a central portion of the back plate 108 may flex in the presence of excessive force, thereby absorbing some of the force. For example, as a plunger of a chest compression device is pressed into the patient's chest, some force is transmitted through the patient to the back plate 108. The back plate 108 may be configured to bend away from the patient if this transferred force exceeds a threshold. This allows for the delivery of compression at the appropriate depth for patients with differing chest wall sizes and stiffness's. This helps prevent broken ribs and/or other injuries to the patient caused by too much force being applied to the patient's chest, as the flexing back plate 108, rather than the ribs or other body structures, absorbs a significant portion of the excess force. Such a design is particularly useful when the elevation device is used in conjunction with a chest compression device such as the LUCAS device, sold by Physio-Control, Inc. and/or the Defibtech ARM.

Figure 1G:
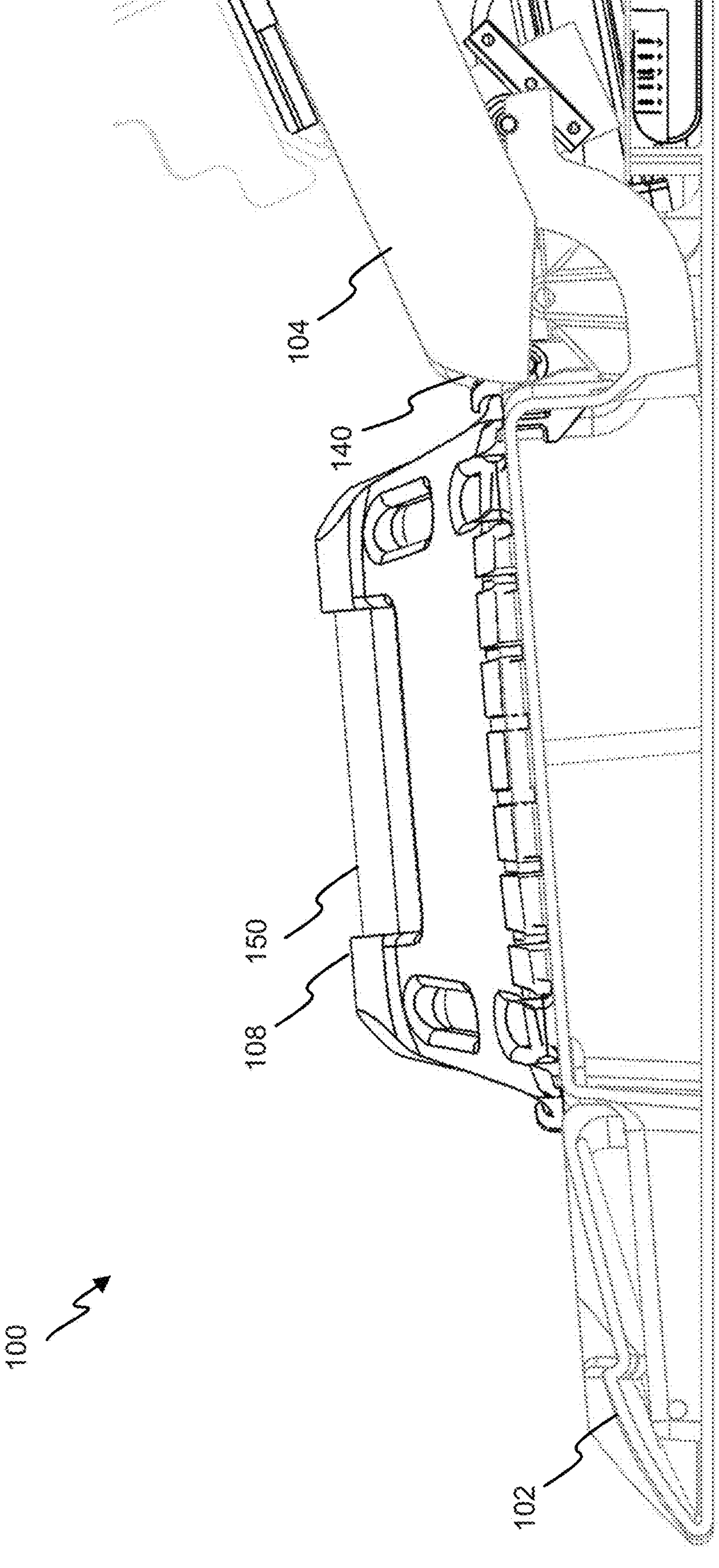
FIG. 1G depicts the head up CPR system of FIG. 1A in a lowered position.
Figure 1H:
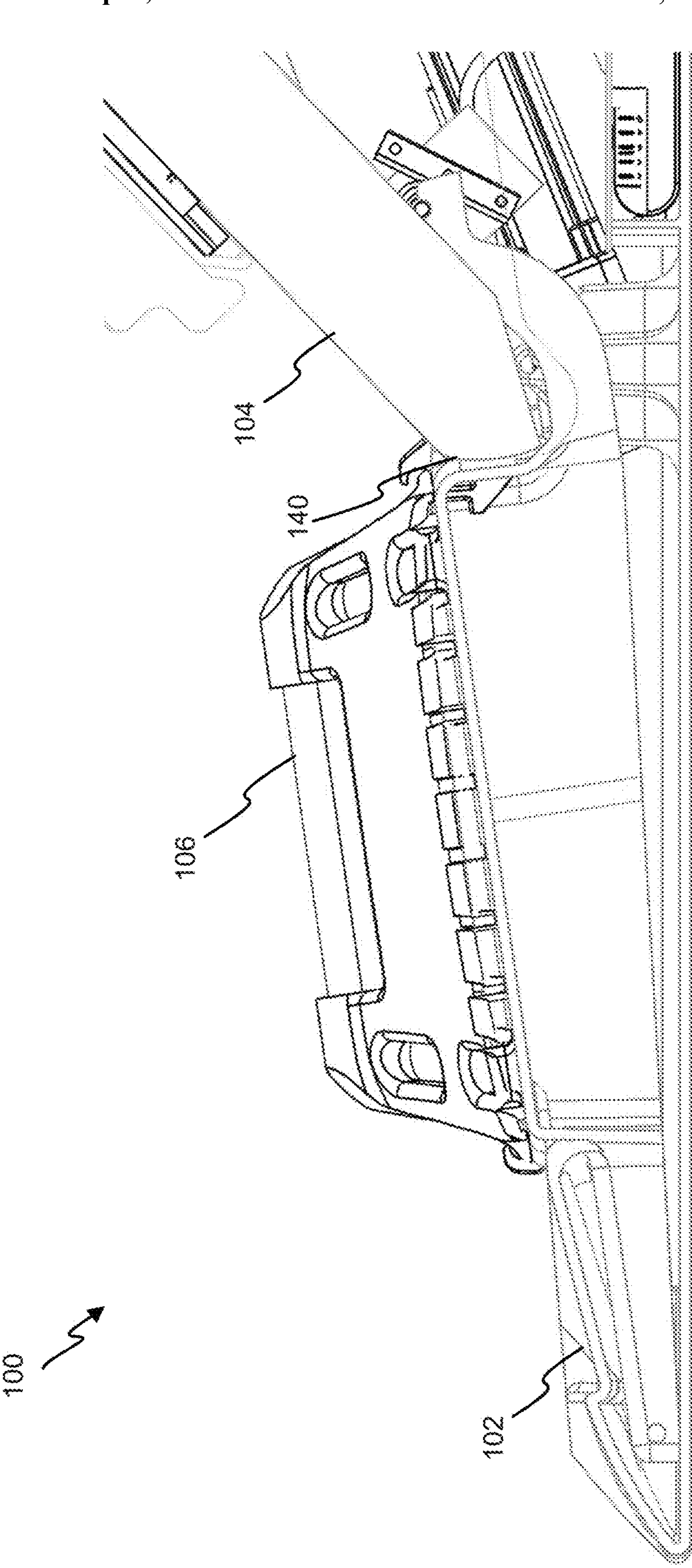
FIG. 1H depicts the head up CPR system of FIG. 1A in an elevated position.

In some embodiments, the back plate 108 that is part of and/or is coupled with the upper support 104 in such a manner that an angle of the back plate 108 is adjustable relative to the base 102 and/or the upper support 104. The back plate 108 may be configured to adjust angularly to help combat thoracic shift to help maintain a chest compression device at a generally orthogonal to the sternum. The adjustment of the back plate 108 may create a separate elevation plane for the heart, with the head being elevated at a greater angle using the upper support 104 as shown in FIG. 1B. In some embodiments, the back plate 108 may be adjusted independently, while in other embodiments, adjustment of the back plate 108 is tied to the elevation of the upper support 104. For example, a back plate may include a roller (such as a v-groove bearing) positioned on an elevation track formed on or coupled with an underside of an upper support. The roller may be positioned on a forward, raised portion of the elevation track. As the upper support 104 is elevated, the roller is forced upward by elevation track, thereby forcing an end of the back plate 108 proximate to the upper support 104 upwards. This causes the back plate 108 to tilt, thus maintaining the chest at a generally orthogonal angle relative to the chest compression device that is coupled with the back plate 108. Oftentimes, elevation track may be slanted from a raised portion proximate to the back plate 108 to a lowered portion. The elevation track may be tilted between about 4° and 20° to provide a measured amount of tilt relative to the thoracic shift expected based on a particular elevation level of the upper support 104. Typically, the back plate 108 will be tilted at a lower angle than the upper support 104 is inclined. Such simultaneous movement is also demonstrated in FIGS. 1G and 1H. In FIG. 1G, the upper support 104 is in the lowered position and the back plate 108 is in its original position. In FIG. 1H, the upper support 104 is elevated, which has caused the back plate 108 to have a corresponding forward tilt, which is less that than the degree of elevation of the upper support 104.

Figure 1I:
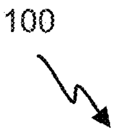
FIG. 1I depicts a latch of the head up CPR system of FIG. 1A.
Figure 1I:
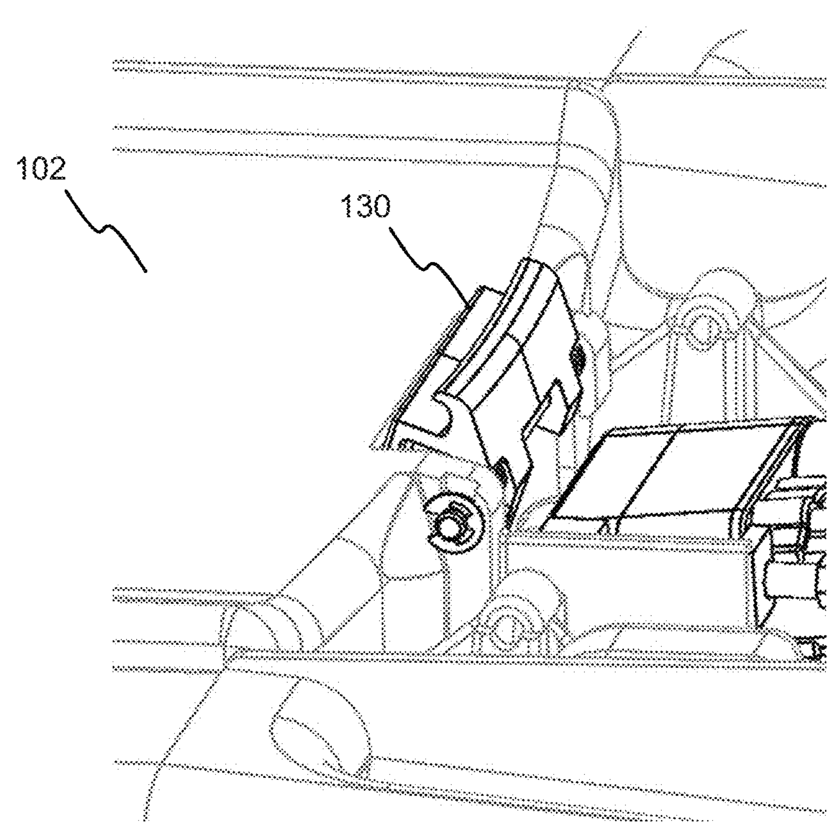
Figure 1J:
FIG. 1J depicts the latch of the head up CPR system of FIG. 1A.
Figure 1J:
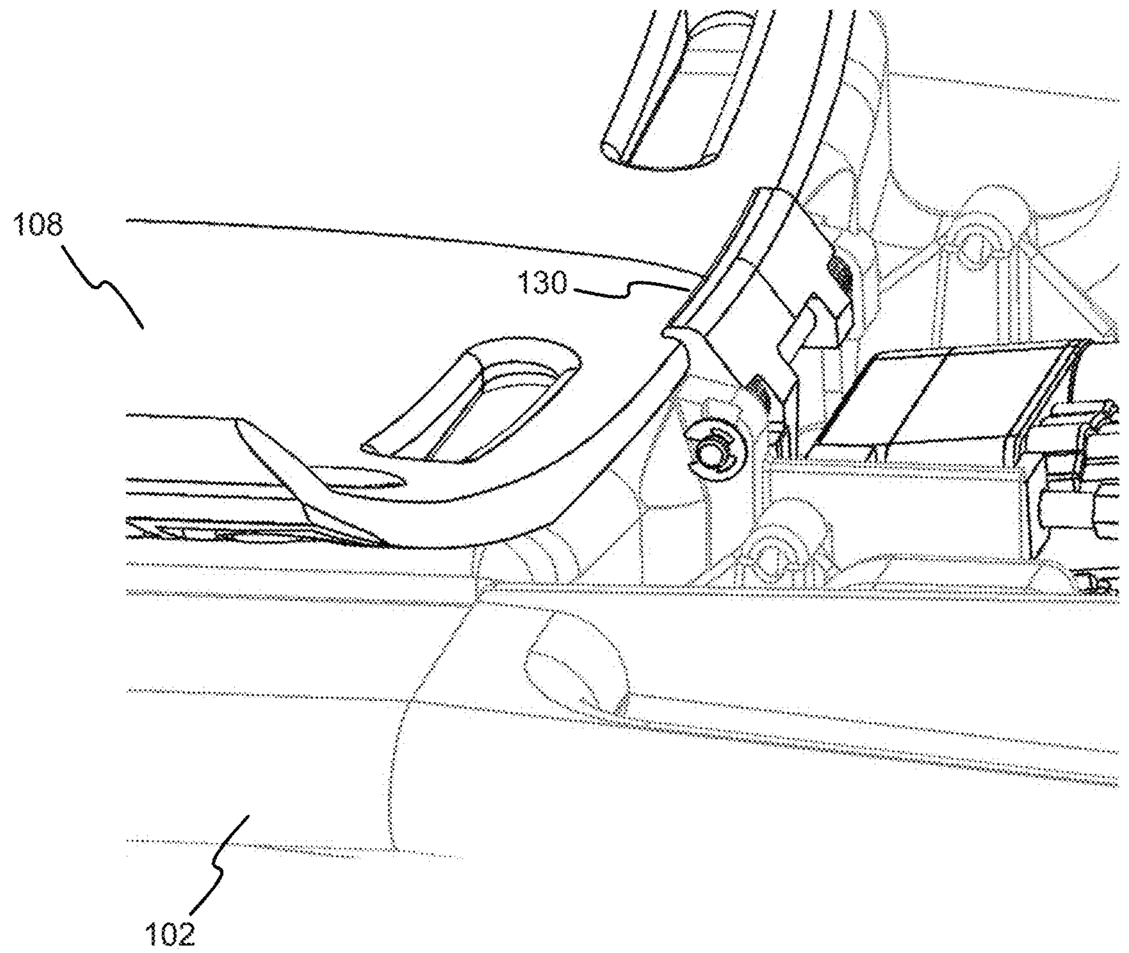
Figure 1K:
FIG. 1K depicts a release knob of the head up CPR system of FIG. 1A.
Figure 1K:
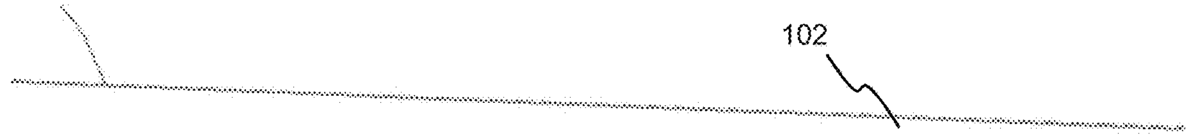
Figure 1K:
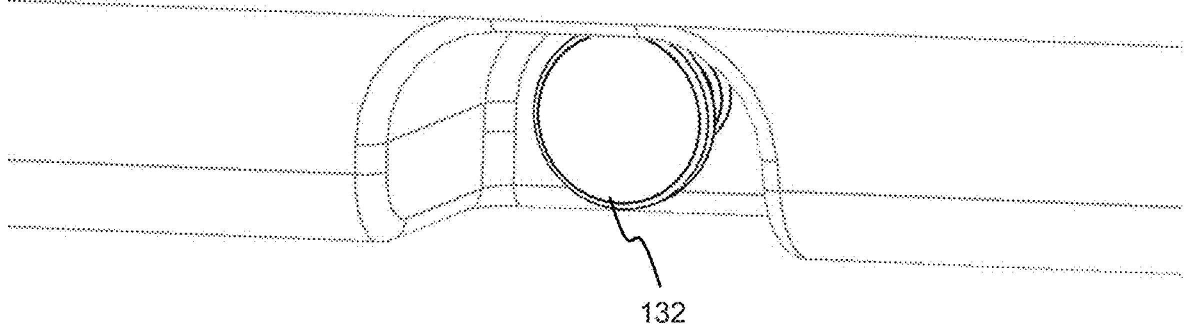
Figure 1L:
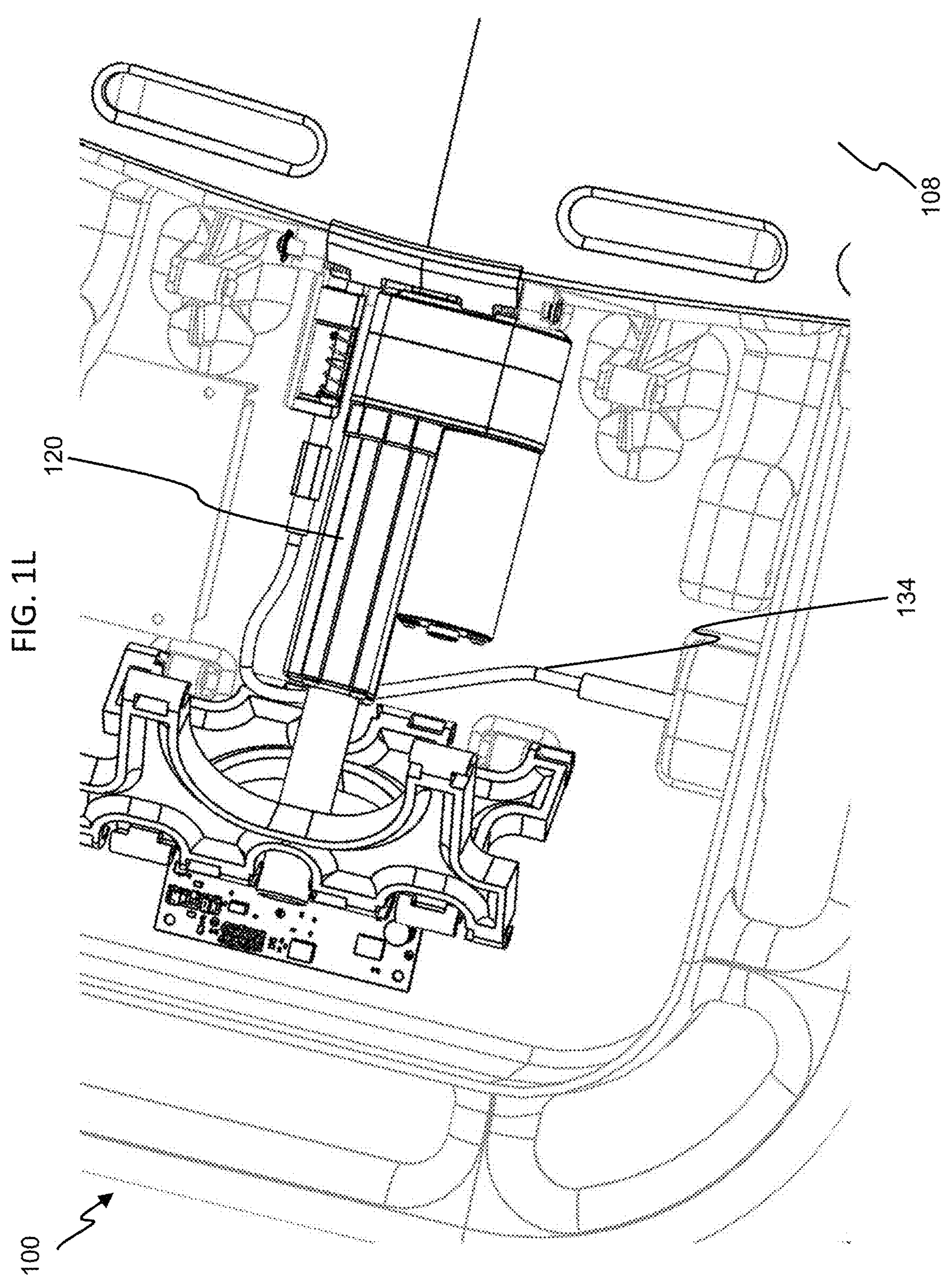
FIG. 1L depicts a release cable of the head up CPR system of FIG. 1A.

In some embodiments, the back plate may be removably coupled with the base 102 and/or the upper support 104. As shown in FIG. 1I, a latch 130 is provided beneath the back plate 108. The latch 130 may be spring biased such that a bottom surface of the latch 130 is able to receive a back edge of the back plate 108. The latch 130 may be pushed downward with the back plate 108 secured by a tip of the latch 130 until a spring-biased pin (not shown) slides along a bottom surface of the latch 130 and engages with a hole formed within a body of the latch 130. The pin secures the latch 130 in a locked position in which the back plate 108 is securely coupled with the base 102 and/or upper support as shown in FIG. 1J. A release knob 132 shown in FIG. 1K is coupled with the base 102 and may be used to draw the pin out of the hole formed in the body of latch 130 to release the back plate 108. For example, as shown in FIG. 1L, release knob 132 may be coupled to the pin via a flexible cable 134, similar to a brake cable on a bicycle. When knob 132 is pulled, the pin is drawn out of the hole and the spring force can push the latch 130 into a release position in which the back plate 108 may be removed from the base 102.

In some embodiments, the HUP CPR system 100 may include a number of features that make the device more safe to operate. For example, as seen in FIG. 1A, HUP CPR system 100 may include a vinyl (or other natural or synthetic material) cover 136 that may cover the moving components, such as the motor or actuator and/or slide mechanism. the cover 136 can extend and retract as the upper support 104 raises and lowers. For example, cover 136 may operate in a manner similar to a convertible top for an automobile, and may retract in a compact, accordion style manner when the upper support 104 is lowered. The upper support 104 of HUP CPR system 100 may have a front surface 140 that is curved in a manner such that as the upper support 104 raises and lowers the front surface 140 stays approximately the same distance from the back plate 108. In other words, a gap between the two components remains generally constant, which eliminates any possible pinching hazard that could exist due to the relative movement between the two components.

In one embodiment, a controller and/or control system may adjust an actuation speed of a motor or other elevation mechanism to raise or lower the upper support 104 of the HUP CPR system 100 within the necessary time frame. For example, medical personnel may set a desired elevation time, starting elevation angle, intermediate elevation angle(s), final elevation angle, rate of elevation, etc. The controller will then operate linear actuator 120, a motor, and/or other elevation mechanism to slowly raise the upper support 104 from a starting elevation angle to a final elevation angle over the selected time period. For example, the controller may be configured to elevate the head and thorax may be done in a sequence by 1) elevating the head and thorax over two or more sequential elevation steps and/or 2) elevating the head and thorax over a more prolonged period of time from the start of the elevation to the final height. In some embodiments, the controller may cause the chest compression device to perform CPR for a period of time (between about 30 seconds and 10 minutes, more commonly between about 2 minutes and 8 minutes, and more commonly between about 3 minutes and 6 minutes) while the individual is in a flat, supine position (or nearly supine, such as with the head and/or heart elevated slightly to an angle of less than about 5 degrees relative to horizontal) prior to causing the actuator to elevate the upper support 104 and the individual to an intermediate and/or final height. In some embodiments where the individual has been primed flat, the controller may perform an additional priming step at an intermediate elevation position prior to elevating the individual to the final/highest elevation position. In other embodiments, the individual may be primed by first elevating the individual's head and heart to one or more intermediate elevation positions (i.e. between about 10 and 25 degrees) and then performing chest compressions for a period of time prior to elevating the individual's heart and head to a final elevation position (i.e. between 20 and 45 degrees). The chest compressions may be continued during the elevation adjustment periods after each priming step.

The controller may also control the rate of elevation of the upper support 104. As just one example, the controller may maintain the elevation speed at a rate of not faster than 10 over each 3 second period. The lift speed may be linear and/or non-linear throughout each elevation step.

Blood drains rapidly from the head when the patient has no blood pressure and the head and upper body are elevated. As a result, there is a need to lower the head fairly rapidly to prevent blood loss in the brain if CPR is stopped while the head is elevated. Typically, this means that the patient's head and upper body may be elevated at a different rate than it is lowered. The patient's head may be lowered by the controller between about 1 and 10 seconds, and typically between about 2-8 seconds.

The controller may also be configured to cause the actuator to slowly and continuously raise the upper support 104 (and individual's heart, shoulders, and head) from a starting elevation position to a final elevation position. For example, a starting elevation position may include the individual being positioned in a generally flat, supine position (with the head elevated less than 5° relative to horizontal). The individual's head, shoulders, and heart may be slowly raised (linearly and/or non-linearly) from the starting elevation position to a position where the head is elevated between about 20 and 45 degrees relative to horizontal (an absolute elevation of the heart by about 5-10 cm and an absolute elevation of the head by about 15-25 cm, although these ranges may vary based on the age, size, and/or physiology of a specific individual) over a period of between about 20 seconds and 10 minutes, more commonly between 1 minute and 4 minutes, more commonly between 1 minute and 2 minutes, and optimally between about 90 seconds and 2 minutes, while CPR is performed. For example, the head, shoulders, and heart may be raised at a rate of between about 2.25°/second and about 1.5°/minute. In other embodiments, an individual may be quickly raised to a starting elevation position of between about 8-15 degrees before slowly elevating the head, shoulders, and heart to a final elevation position over a period of between about 30 seconds and 10 minutes, more commonly between 2 minutes and 8 minutes, and optimally between about 3 minutes and 6 minutes, while CPR is performed.

In some embodiments, the controller may receive data from one or more physiological sensors and use this data to determine rates and timing of elevation and lowering. For example, the patient on the HUP CPR system 100 may be monitored using an electrocardiogram (ECG). The ECG may detect a stable heart rhythm even if the individual has no palpable pulse. Based on this detection of the stable heart rhythm, it may be determined to stop the performance of chest compressions and to promptly lower the upper support 104. For example, once it is detected that the patient has a stable heart rhythm, the controller may alert medical personnel that chest compressions should be ceased, and may send a signal to the motor or other actuator to cause the upper support 104 to rapidly lower. In some embodiments, alerting medical personnel may involve producing a visual indicator, such as lighting up a light emitting diode (LED) or other light source and/or presenting a textual and/or image-based display on a screen of the HUP CPR system 100. In one embodiment, upon detecting a stable heart rhythm, the controller may send a command to the automatic chest compression device that causes the chest compression device to stop the delivery of chest compressions and/or decompressions. In another embodiment, upon detecting the stable heart rhythm, the controller will alert medical personnel, who may then operate the HUP CPR system 100 to lower the upper support 104. It will be appreciated that other sensors may be used in conjunction with the HUP CPR system 100 to determine: when to start and/or stop CPR, when to elevate and/or lower a patient's upper body, a degree of elevation of the patient's upper body, a rate of elevation or lowering of the patient's upper body, and/or other parameters of CPR and/or ITPR.

The HUP CPR system 100 elevates the head above the heart, with the level of elevation optionally varying depending upon the method of CPR. Conventional closed chest manual CPR itself is inherently inefficient, providing only about 20% of normal blood flow to the heart and brain. Elevation of the head is not safe during conventional CPR as it is not possible to consistently or safely push enough blood "uphill" to the head to take advantage of the effects of gravity of the venous side of the arterial-venous circuit that is integral to cerebral perfusion. Methods of CPR that generate the most forward flow provide the opportunity to elevate the head above the heart more than those methods that provide less forward flow. For example, active compression decompression (ACD) CPR with an impedance threshold device (ITD) can triple blood flow to the heart and brain compared with conventional manual CPR alone and therefore the head can be elevated higher and still get enough perfusion to take advantage of the effects of gravity with HUP CPR. By contrast, the head should not be elevated as much with conventional CPR and the ITD as forward blood flow without ACD CPR is less, and therefore too much elevation of the head could worsen outcomes. For these reasons the optimal head elevation may vary both depending upon the method of CPR used and the condition of the patient.

The relative vertical distance between the head and the heart is important as the amount of pressure needed to "lift" or pump the blood from the heart to the brain is related to this distance. Further, the vertical distance between the head and the heart affects the amount of cerebral perfusion. Although the amount of elevation of the head relative to the heart may vary depending upon the method of CPR (which is the mechanism used to pump the blood), it is generally preferred to have the head elevated relative to the heart by a distance in the range from about 2 cm to about 42 cm. In the specific case where ACD-CPR is being performed with an ITD, the distance may be in the range from about 5 cm to about 25 cm, for standard CPR with an ITD between about 5 cm and about 20 cm, for ACD CPR by itself between about 5 cm and about 20 cm, and with conventional or standard CPR between about 3 cm and about 15 cm. Further, the distance that the heart may be elevated relative to a support surface upon which the lower portion of the patient is resting (such as a table, floor, gurney, stretcher, or the ground) may be in the range from about 3 cm to about 20 cm (with ranges between about 4 cm and 10 cm being common), while the height of the head relative to the support surface may be in the range from about 5 cm to about 45 cm (with ranges between about 10 cm and 40 cm being common). When performing ACD-CPR+ITD, the distance that the heart may be elevated relative to a support surface upon which the patient is resting may be in the range from about 3 cm to about 20 cm, while the height of the head relative to the support surface may be in the range from about 5 cm to about 45 cm. Of course, these relative heights can also be thought of in terms of an angle of elevation of the upper body relative to the lower body when the patient is bent at the waist when performing CPR. Such angles are described herein. Typically, the angle between the patient's heart and brain is between 10 degrees and 40 degrees relative to horizontal to achieve the necessary elevation, although it will be appreciated that such angles are largely driven by the patient's physiology (height, distance between head and heart, etc.).

In some embodiments the heart will not be elevated. For example, a small head-only elevation device may be used that would only elevate the head, while allowing the heart to remain in the horizontal plane along with the lower body. Such elevation devices may be particular useful when performing CPR without the use of a CPR assist device/automated chest compression device as it reduces the amount of force needed to pump blood to the patient's brain during CPR. In such cases, the head would be raised to a distance in the range from about 5 to 20 cm relative to the heart (which is not elevated relative to the support surface).

In some embodiments, the controller be configured to detect a type of CPR being delivered and may automatically adjust an elevation of the heart and/or head based on the detected level of force. This may be done, for example, by allowing a user to input a type of CPR being performed into the HUP CPR system 100. In other embodiments, such as those where a chest compression device is coupled with or formed integrally with the HUP CPR system 100, the HUP CPR system 100 may communicate with the chest compression device to determine if the chest compression device is being used to deliver compressions and/or an amount of force being delivered and may make any necessary elevation adjustments based on this data. In other embodiments, one or more physiological sensors may be used to detect physiological parameters, such as cerebral perfusion pressure, intrathoracic pressure, and the like. This sensor data may be used to determine a compression force and/or otherwise determine how high to elevate the head and heart.

During HUP CPR, the effect of gravity on draining blood back to the heart after each compression may vary as the elevation of the patient's upper body is changed. This physiology may necessitate varying the negative pressure or force applied to the chest as the head, heart, and shoulders are further elevated in order to generate sufficient arterial blood flow to the brain as the patient is elevated during HUP CPR. Therefore, the amount of negative pressure may need to be varied throughout the performance of HUP CPR to account for the changing elevation of the heart and head to ensure that a sufficient amount of blood is drawn back into the heart after each compression. In some embodiments, to account for the changes to the required level of negative pressure at different elevations of HUP CPR, a chest compression device may be configured to vary the amount of active decompression applied to the patient's chest based on the elevation angle of the heart and/or head of the individual. This may include decompressing further, faster, or for a longer period of time over the course of the compression decompression cycle.

Similarly, during HUP CPR, the physiology may necessitate varying the positive pressures in the chest as the head, heart, and shoulders are further elevated in order to generate sufficient arterial blood flow to the brain as the patient is elevated during HUP CPR. Therefore, the amount of positive pressure or force may need to be varied throughout the performance of HUP CPR to account for the changing elevation of the heart and head to ensure that a sufficient amount of blood is drawn back into the heart after each compression. In some embodiments, to account for the changes to the required level of positive pressure or force at different elevations of HUP CPR, a chest compression device may be configured to vary the amount of active compression applied to the patient's chest based on the elevation angle of the heart and/or head of the individual. This may include compressing further, faster, or for a longer period of time over the course of the compression decompression cycle.

Figure 1M:
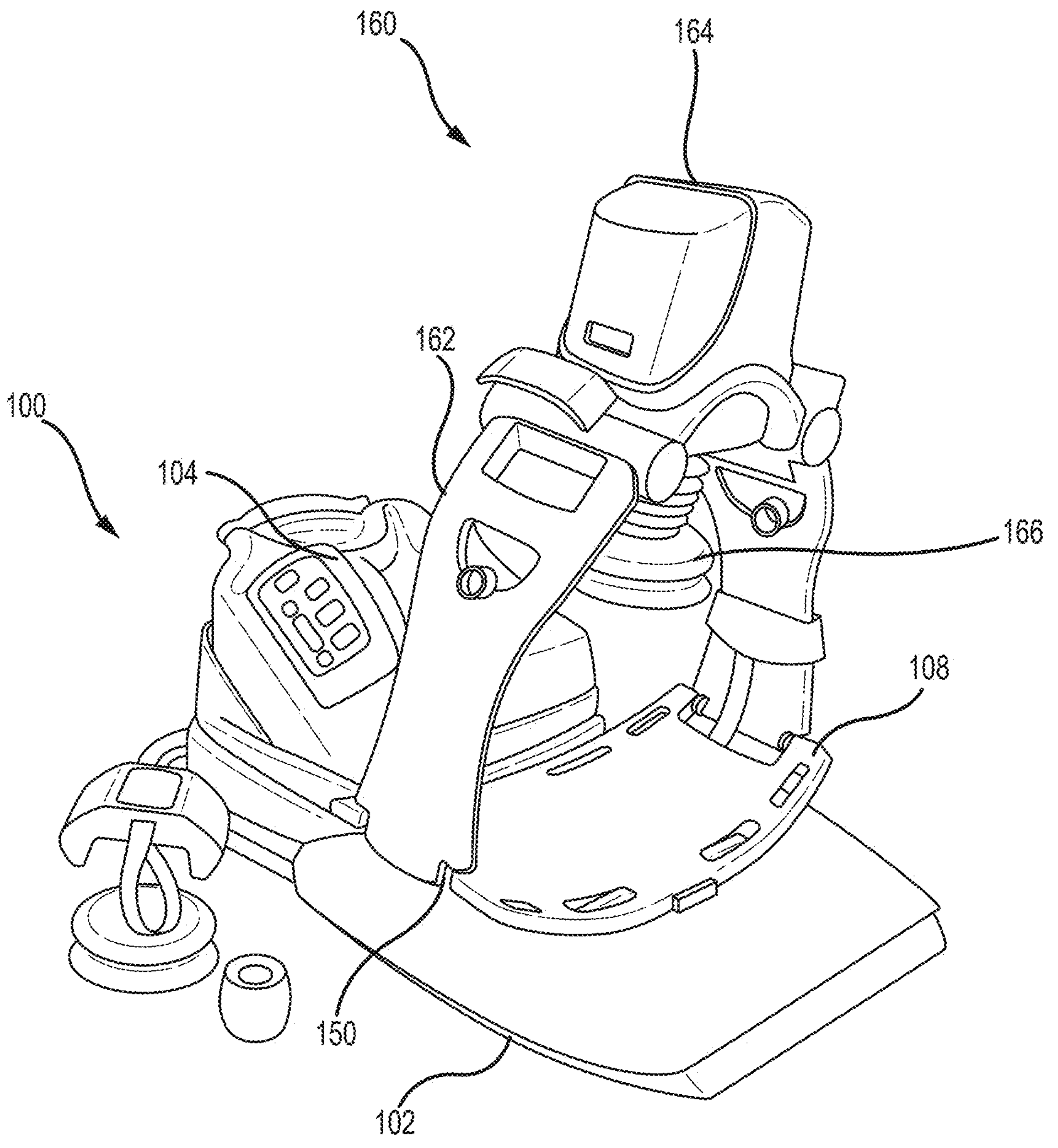
FIG. 1M depicts the head up CPR system of FIG. 1A coupled with a chest compression device.

FIG. 1M illustrates HUP CPR system 100 coupled with a chest compression device 160. The chest compression device 160 may be attached to the HUP CPR system 100 using the coupling 150 and/or using other coupling mechanisms. The chest compression device 160 may include one or more supports 162 that elevate and maintain a compression unit 164 above an individual's heart. The compression unit 164 may include a patient interface 166 that may be positioned against and/or attached to the individual's chest and apply force from the compression unit 164 to repeatedly compress the individual's chest. In some embodiments, the patient interface 166 may include a suction cup and/or adhesive pad, enabling the compression unit 164 to exert a pulling force on the individual's chest that actively decompresses the chest to ensure that a sufficiently large chest recoil occurs after each chest compression. In some embodiments, the chest compression device 160 may be permanently fixed to the HUP CPR system 100, while in other embodiments the chest compression device 160 may be removably attached. The chest compression device 160 may be controlled using a user interface. The user interface may be on the chest compression device 160 and/or on the HUP CPR system 100. The user interface may enable a timing, depth, and/or rate of chest compressions and/or decompressions to be adjusted.

Figure 2A:
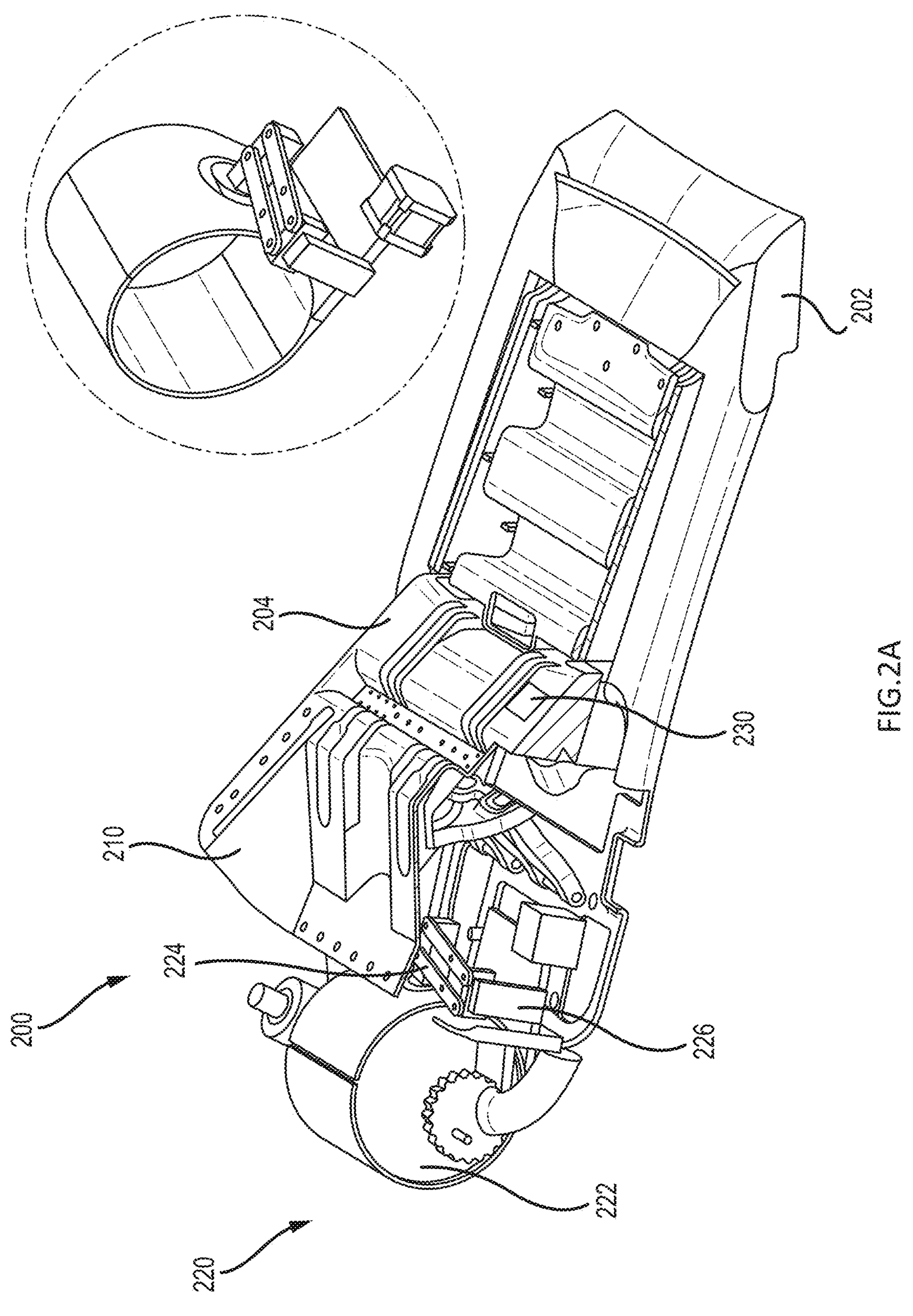
FIG. 2A depicts a head up CPR system with an integrated positive pressure ventilation device according to embodiments.
Figure 2B:
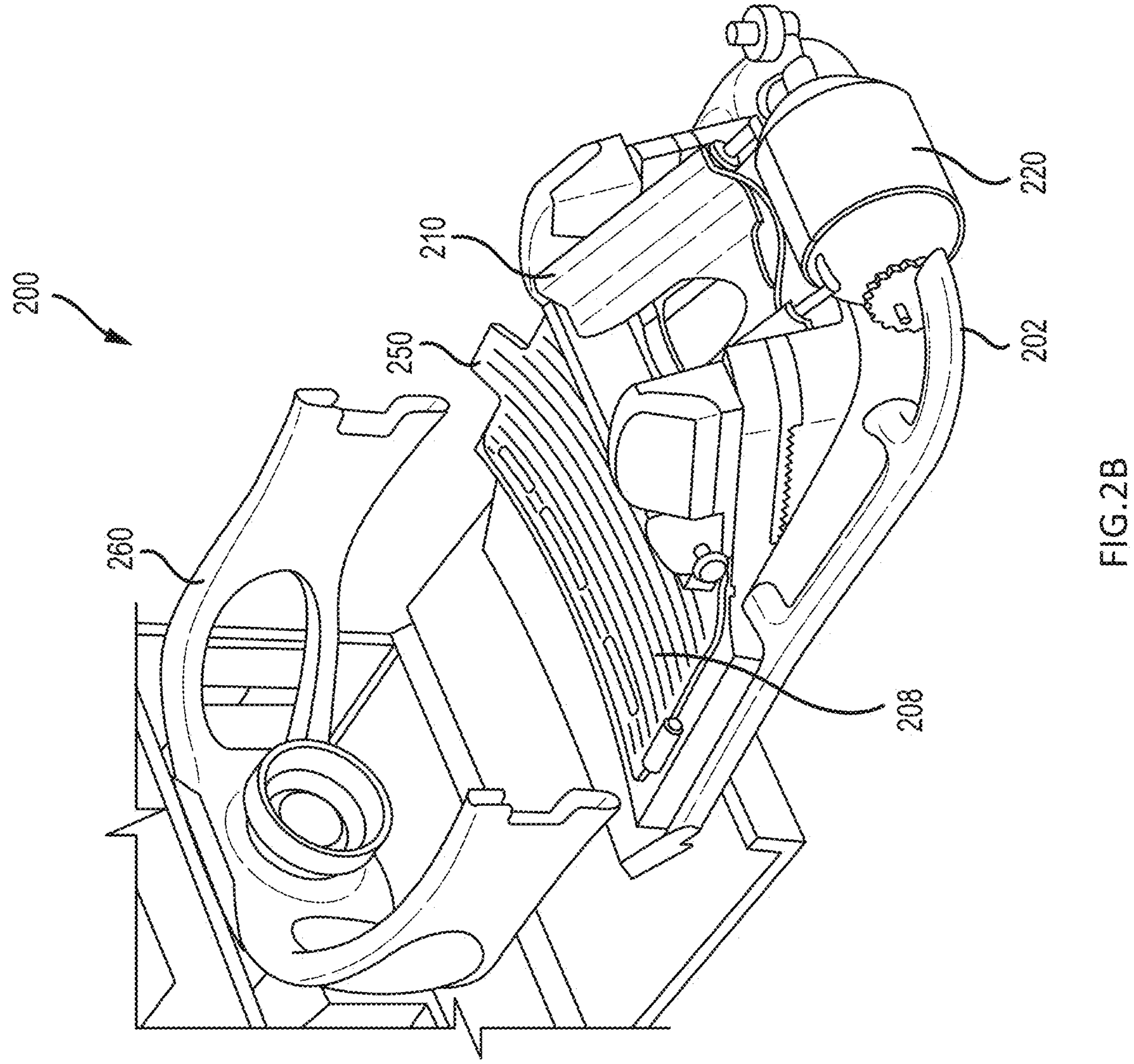
FIG. 2B depicts the head up CPR system of FIG. 2A with a chest compression device.

FIGS. 2A and 2B illustrate another embodiment of a HUP CPR system 200. The HUP CPR system 200 may be similar to HUP CPR system 100 and may include any of the features described above. For example, the HUP CPR system 200 may include a base 202, an upper support 204 that is coupled with the base 202 and configured to move between a lowered position and an elevated position (and any position therebetween). The upper support 204 may include a head-receiving portion 210 that is designed to support the head in the sniffing position to aid in proper ventilation of the individual. A back plate 208 (shown in FIG. 2B) may be coupled with the base 202 and/or upper support 204. The back plate 208 may be removably coupled with the HUP CPR system 200 in some embodiments. The back plate 208 may include a coupling 250 that may receive a chest compression device 260 (shown in FIG. 2B), which may be similar to chest compression device 160 described above. The chest compressions may be performed as continuous uninterrupted chest compressions and/or interrupted chest compressions. For example, the chest compressions may be performed both continuously uninterrupted chest compressions while ventilations are performed simultaneously (e.g., with 1 breath every 10 compressions) or may be paused during delivery of ventilations (e.g., perform 30 compressions followed by 2 breaths). In some embodiments, the chest compression device 260 may be configured to deliver compressions at a variable rate. For example, in some embodiments, the chest compression device 260 may typically deliver compressions at a rate of about 100 compressions/minute. The chest compression device 260 may then be operated to slow down to about 60 compressions/minute for one positive pressure ventilation. This slow in compression rate may be performed one or more times per minute. For example, in some embodiments, the compression rate slowdown may be performed between about 8 and 12 times per minute. In such embodiments, the chest compression device may continuously compress the chest, even while slowing rate, which may enable for full and/or otherwise improved insufflation of the lungs over a period of time, such as 0.5 seconds.

As illustrated, HUP CPR system 200 may include an integrated positive pressure ventilation system 220. For example, the positive pressure ventilation system 220 may be positioned on base 202, such as at a position behind the head-receiving portion 210. The positive pressure ventilation system 220 may include a bellows system that may compress a manual resuscitator bag (a.k.a. Ambu bag) 222 in which breath delivery is initiated through a mechanical linkage system 224 driven by an electric stepper motor 226 or other actuator. The positive pressure ventilation system may be accomplished through other means, including but not limited to, a power turbine-driven positive system, a piston-driven positive pressure ventilation system, and/or a compressed air metering and delivery system.

The positive pressure ventilation pressure ventilation system 220 may be controlled by a microprocessor. In some embodiments, the microprocessor may control of the positive pressure ventilation system 220 using a feedback loop using one or more pressure sensors and/or an accelerometer that are in communication with the motor 226. The positive pressure ventilation system 220 may deliver a specified positive pressure rate, such as about 8 breaths/minute, although this rate may be varied based on user input and/or input from one or more physiological sensors. For example, the delivery rate and/or timing may be varied based on inputs from sensors that measure parameters such as end tidal $CO_2$. In some embodiments, the tidal volume (300-1000 ml) may be pre-set and consistent with AHA guidelines (500 ml) to further simplify deployment of the positive pressure ventilation system 220. In other embodiments, the tidal volume may be adjustable. The positive pressure rate may be adjustable once a return of spontaneous circulation is achieved, which may help to accommodate transport. A duration of each positive pressure ventilation may be varied between about 200 msec and 1500 msec, more commonly between about 300 msec and 1200 msec. The positive pressure ventilation system 220 may be a volume-controlled ventilator, a pressure-controlled ventilator, and/or a combined pressure/volume-controlled ventilator. In some embodiments, various operational parameters of the positive pressure ventilation system 220, such as the tidal volume, pressure, duration, rate, etc., may be automatically adjusted based on data from one or more physiological sensors, such as end tidal $CO_2$ sensors. The high peak inspiratory pressure limit of the positive pressure ventilation system 220 may be regulated by a standard pop-off valve found in the manual resuscitator bag 222. The positive pressure ventilation system 220 may include an alarm that may alert the caregiver of high peak inspiratory pressures and possible airway obstruction, pneumothorax, and/or airway collapse. In addition, some embodiments may incorporate a pressure sensor and an alarm to alert the caregiver if a potential airway disconnect is present or whether there is a lack of negative intrathoracic pressure, indicative of the absence of an ITD or an open airway. In some embodiments, the element compressing the bellows system may include a sensor to determine the compressive load or resistance to compression; a high compression force may be indicative of an obstructed airway or improperly loaded bellows system and a low resistance indicative of an open air circuit, and/or lack of a bellows present. The positive pressure ventilation system 220 may be powered by an on-board battery and may utilize a standard airway circuit, enabling the positive pressure ventilation system 220 to be disconnected and utilized with other positive pressure ventilation devices. The manual resuscitation airway system may be utilized to provide manual breath delivery, and then transition to delivery of automated, synchronized compressions without disruption or discontinuity of treatment. The manual resuscitator bag 222 may be easily removable to facilitate bag replacement following each use.

The processor of the positive pressure ventilation system 220 may be in communication with (or be the same processor) as a main processor of the HUP CPR system 200. This enables data related to elevation of the upper support 204, information related to chest compressions and/or decompressions, and/or information related to the delivery of positive pressure ventilations to be communicated between the various subsystems of HUP CPR system 200. This enables data and/or settings of one subsystem to be used to at least partially control the operation of one or more subsystems. For example, the delivery of positive pressure ventilations may be synchronized with the chest compression cycle. In a particular embodiment, delivery of positive pressure ventilations to the chest wall may be synchronized with all or a portion of the decompression phase of CPR. More specifically, the positive pressure ventilation may be primarily timed to be delivered with a phase of CPR based upon a sensed signal, such as when the compression or decompression phase starts or is completed. One or more sensors 230 (e.g. load cell, accelerometer, vibration sensor, magnetic sensor, acoustic sensor, linear transducer, and the like) that are used to synchronize the ventilations may be incorporated into the Head Up CPR device, the backboard, the CPR compression system, and/or the intrathoracic pressure regulation device. In some embodiments, the sensors used for synchronizing the ventilations may be provided as one or more remote sensors that are applied by the user to the Head Up CPR device, the backboard, the CPR compression system, and/or the intrathoracic pressure regulation device. Such synchronization and optimization of breath delivery time may improve cerebral perfusion pressures and minimize high peak inspiratory pressures. High peak inspiratory pressures reduce venous blood flow back to the heart, increase ICP, and can cause lung trauma. In some embodiments, a waveform of the positive pressure ventilation system 220 may be adjusted.

Figure 3:
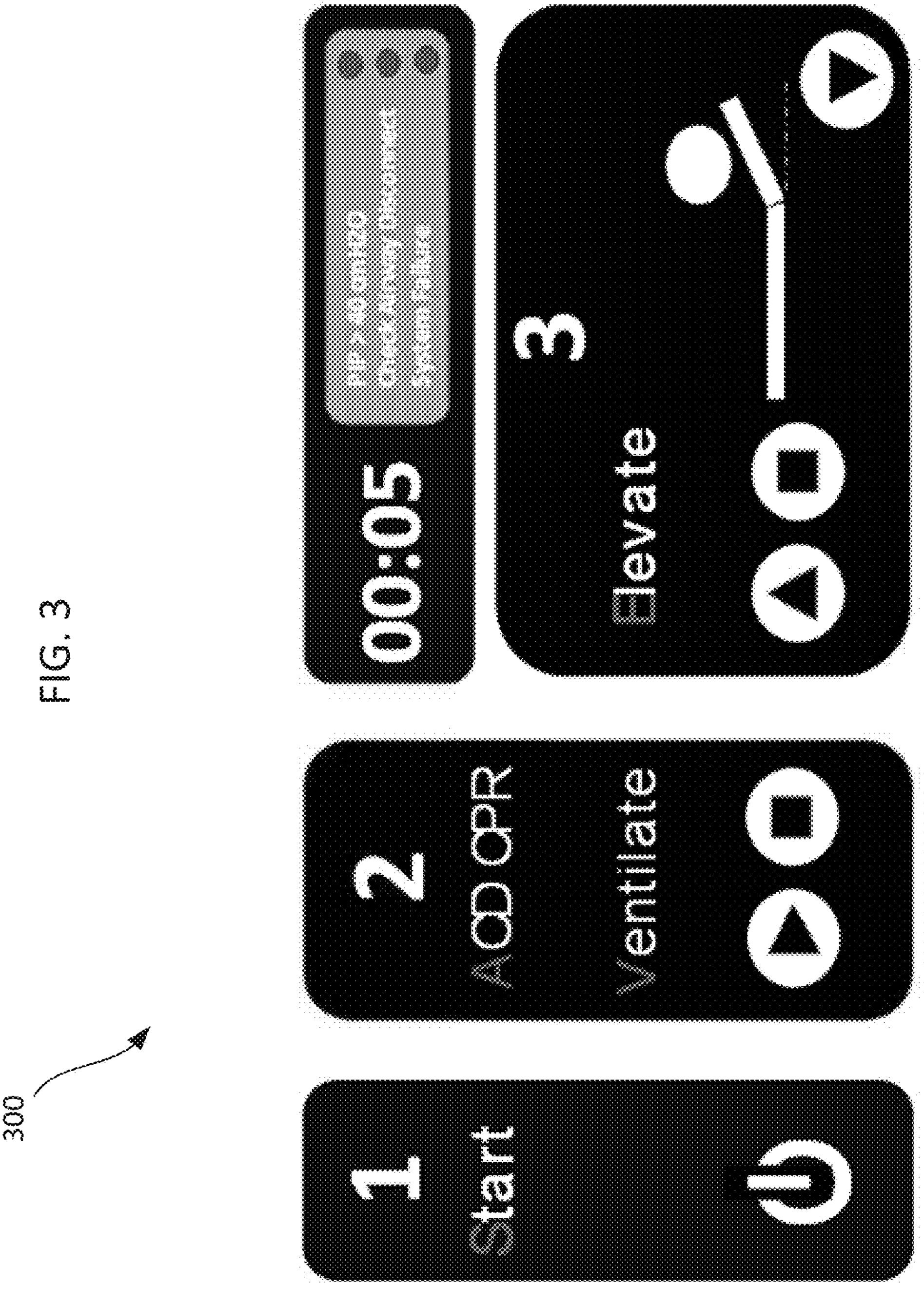
FIG. 3 depicts a user interface of a head up CPR system according to embodiments.

The HUP CPR system 200 may include an interface that may enable a user to set and/or adjust one or more parameters of the elevation of the upper support 204, operation of the chest compression device 260, and/or operation of the positive pressure ventilation system 220. FIG. 3 illustrates one example of an interface 300 that may be provided on a HUP CPR system, such as system 100 or 200. The interface 300 may enable a user to a) initiate ventilation and adjust ventilation settings corresponding settings, b) initiate chest compressions and decompressions and adjust corresponding settings (depth, rate, etc.) and c) initiate and/or elevation (although this feature may be automated based on initiation of chest compressions in some embodiments). Through this control interface, the duration of the breath delivery may be varied, for example, from 200 ms to 2000 ms. Breath delivery may be timed such that the breath delivery is synchronized with the decompression, the compression phase of CPR, or somewhere in the middle.

As discussed above, the positive pressure ventilation system 220 may operate to time the delivery of positive pressure ventilations based on sensing a compression/decompression cycle of CPR. This may be performed alone or in conjunction with the elevation system of the HUP CPR system 200. For example, the positive pressure ventilation system 220 may be interfaced with the airway of a supine patient who is not positioned on the HUP CPR system 200. The positive pressure ventilation system 220 may include or be coupled with one or more sensors that provide measurements and/or other data that indicate a timing of the CPR cycle. For example, sensors coupled with the chest compression device and/or physiological sensors, such as end tidal $CO_2$ sensors, may be used to determine a timing of the CPR cycle. The delivery of the positive pressure ventilations may be initiated based on the sensed data.

Figures 4A, 4B:
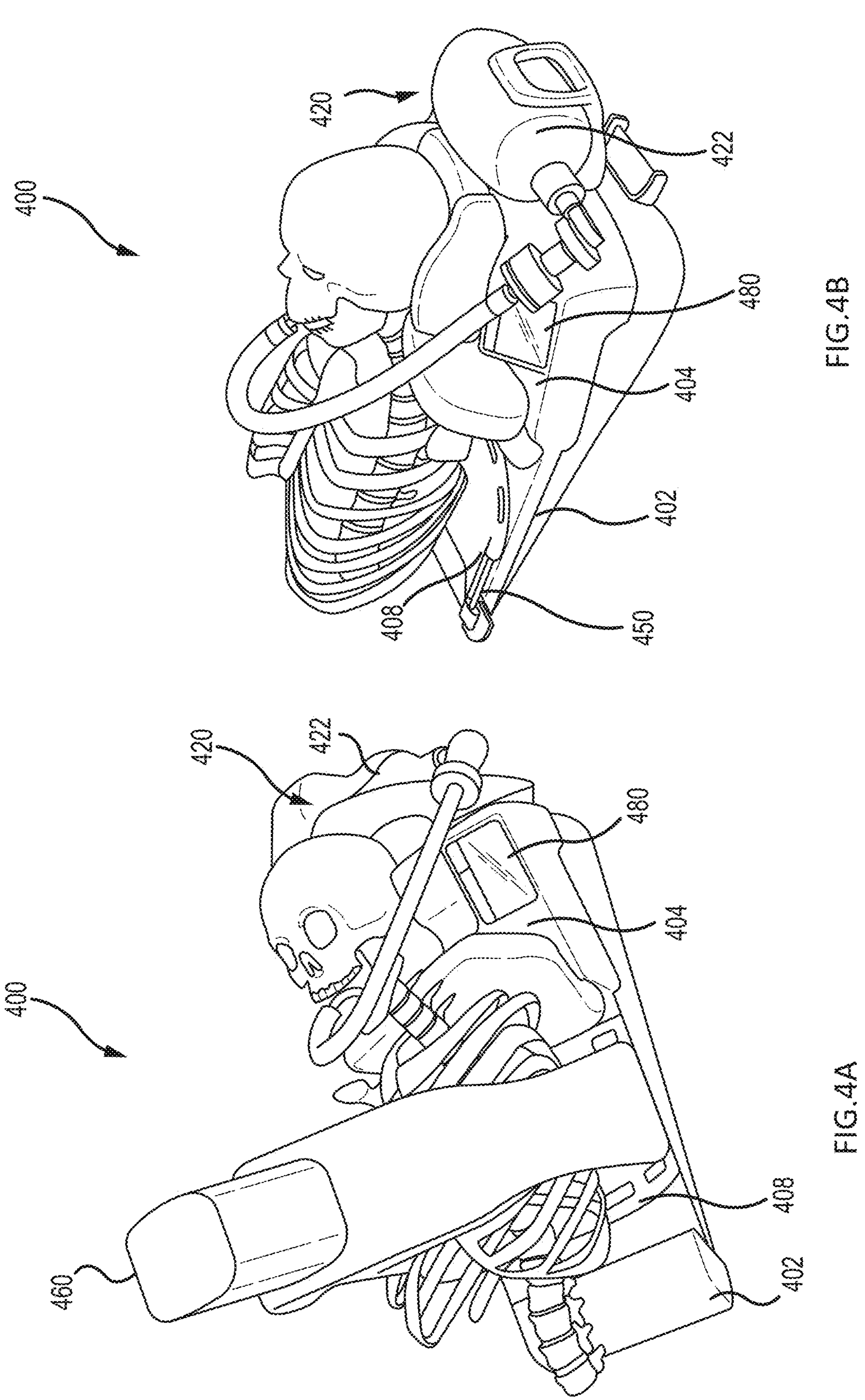
FIG. 4A depicts a head up CPR system with an integrated positive pressure ventilation device according to embodiments.
FIG. 4B depicts the head up CPR system of FIG. 4A.
Figure 4C:
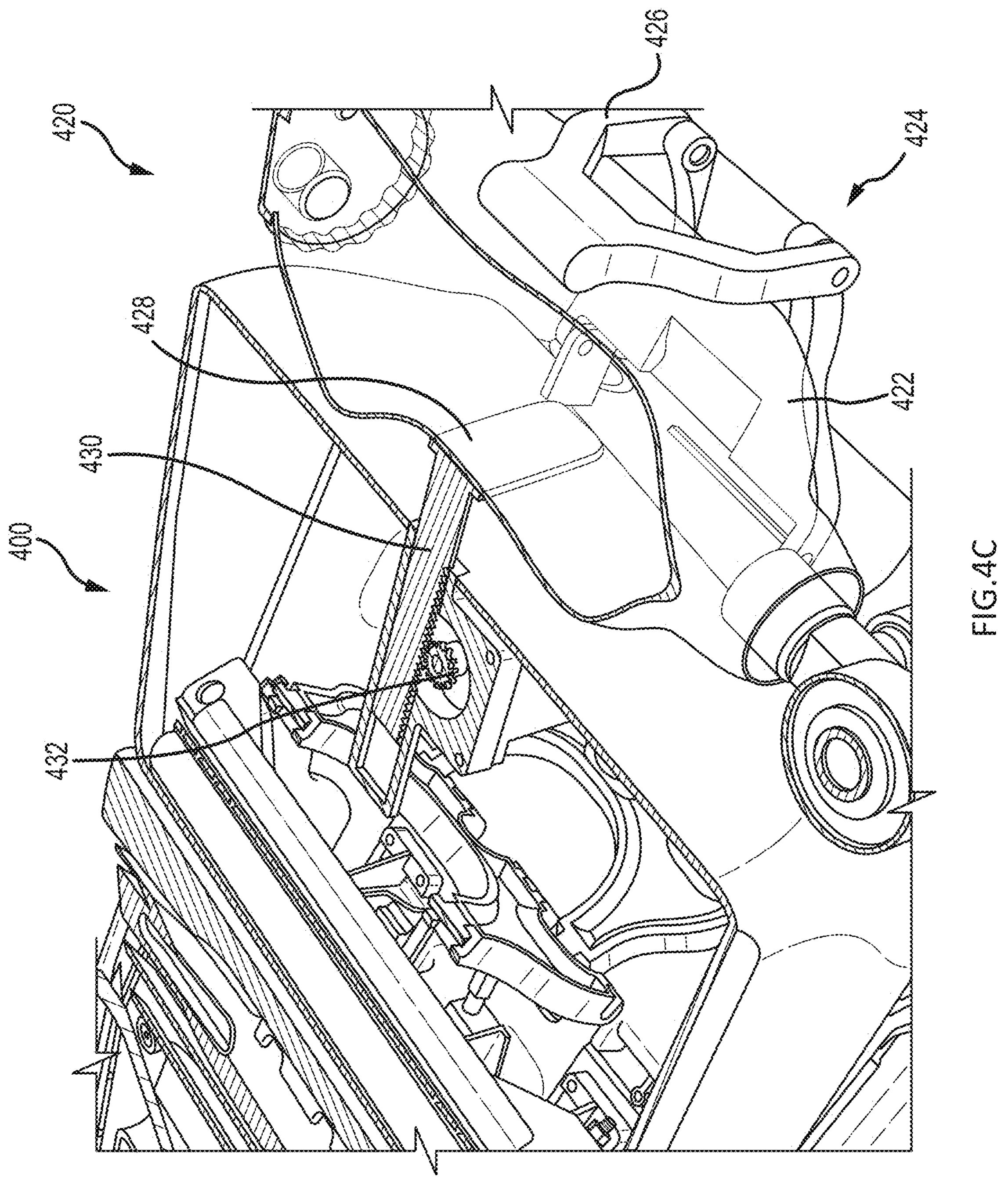
FIG. 4C depicts a cross-sectional view of an automated bag compressor of the head up CPR system of FIG. 4A.

FIGS. 4A-4C illustrate another embodiment of a HUP CPR System 400. HUP CPR system 400 may be similar to HUP CPR systems 100 and 200 described above and may include any of the features described above. For example, HUP CPR System 400 may include a base 402, an upper support 404 that is coupled with the base 402 and configured to move between a lowered position and an elevated position (and any position therebetween). A back plate 408 may be coupled with the base 402 and/or upper support 404. The back plate 408 may include a coupling 450 that may receive a chest compression device 460, which may be similar to chest compression devices 160 and 260 described above. HUP CPR system 400 may include an integrated positive pressure ventilation system 420. The HUP CPR system 400 may also include an interface 480 that may enable a user to set and/or adjust one or more parameters of the elevation of the upper support 404, operation of the chest compression device 460, and/or operation of the positive pressure ventilation system 420.

In some embodiments, the positive pressure ventilation system 420 of HUP CPR system 400 may include a manual resuscitator bag 422 that can be connected to or uncoupled from a mechanical bag squeezer 424. The resuscitator bag squeezer 424 may be regulated by a controller and may be coupled to one or more sensors and/or processors to vary the timing of the breath, the duration of the breath, the waveform of the breath, and/or the frequency of the breath delivered. The resuscitator bag 422 may be squeezed by hand or inserted into the automated bag squeezer 424. The resuscitator bag 422 may be transitioned by the user from one mode to the next without disruption of breath delivery. For example, a user may first start delivery of positive pressure ventilations by manually squeezing the resuscitator bag 422 and then place the resuscitator bag 422 into the automated bag squeezer 424, which may then be activated to initiate automated delivery of positive pressure ventilations without any disruption in the delivery of ventilations. In other instances, the delivery of positive pressure ventilations may be automated first, and then a user may remove the resuscitator bag 422 from the automated bag squeezer 424 and then commence with manual squeezing of the resuscitator bag 422. It will be appreciated that other embodiments to deliver an automated breath are also possible including mechanical breath delivery systems based upon a piston mechanism (e.g., a syringe that reciprocates mechanically to deliver a positive pressure breath), a turbine, a blower, bellows, compressed air metering, and the like.

As best illustrated in FIG. 4C, in some embodiments, the automated bag squeezer 424 may include a fixed support 426. In some embodiments, the fixed support 426 may be positioned at a distal end of the HUP CPR system 400. The automated bag squeezer 424 may also include a movable support 428 that is positioned opposite the fixed support 426. The moveable support 428 may be translatable toward and away from the fixed support 426 such that when resuscitator bag 422 is positioned between the supports, movement of the moveable support 428 causes the resuscitator bag 422 to contract and expand to deliver positive pressure ventilations to a patient. The moveable support 428 may be translated using any number of electrical and/or mechanical mechanisms. In one particular embodiment, the movable support 428 may be translated by a rack and pinion connection that is driven by a motor. For example, the moveable support 428 may include or otherwise be coupled with a rack 430 that defines a number of teeth. A motor (not shown) may be coupled with and configured to drive a pinion 432. Teeth of the pinion 432 may be engaged with the teeth of the rack 430 such that rotation of the pinion 432 causes the rack 430 (and subsequently moveable support 428) to reciprocate along a translation axis of the rack 430. The motor may alternately rotate the pinion 432 in clockwise and counterclockwise directions to reciprocate the moveable support 428. The motor may be coupled with one or more controllers and/or sensors that may control various variables of operation, such as a specified positive pressure rate, a timing of positive pressure ventilations, and the like. It will be appreciated that the positions of the fixed support 426 and/or moveable support may be switched or otherwise altered. Additionally in some embodiments, both supports may be moveable.

Figure 5:
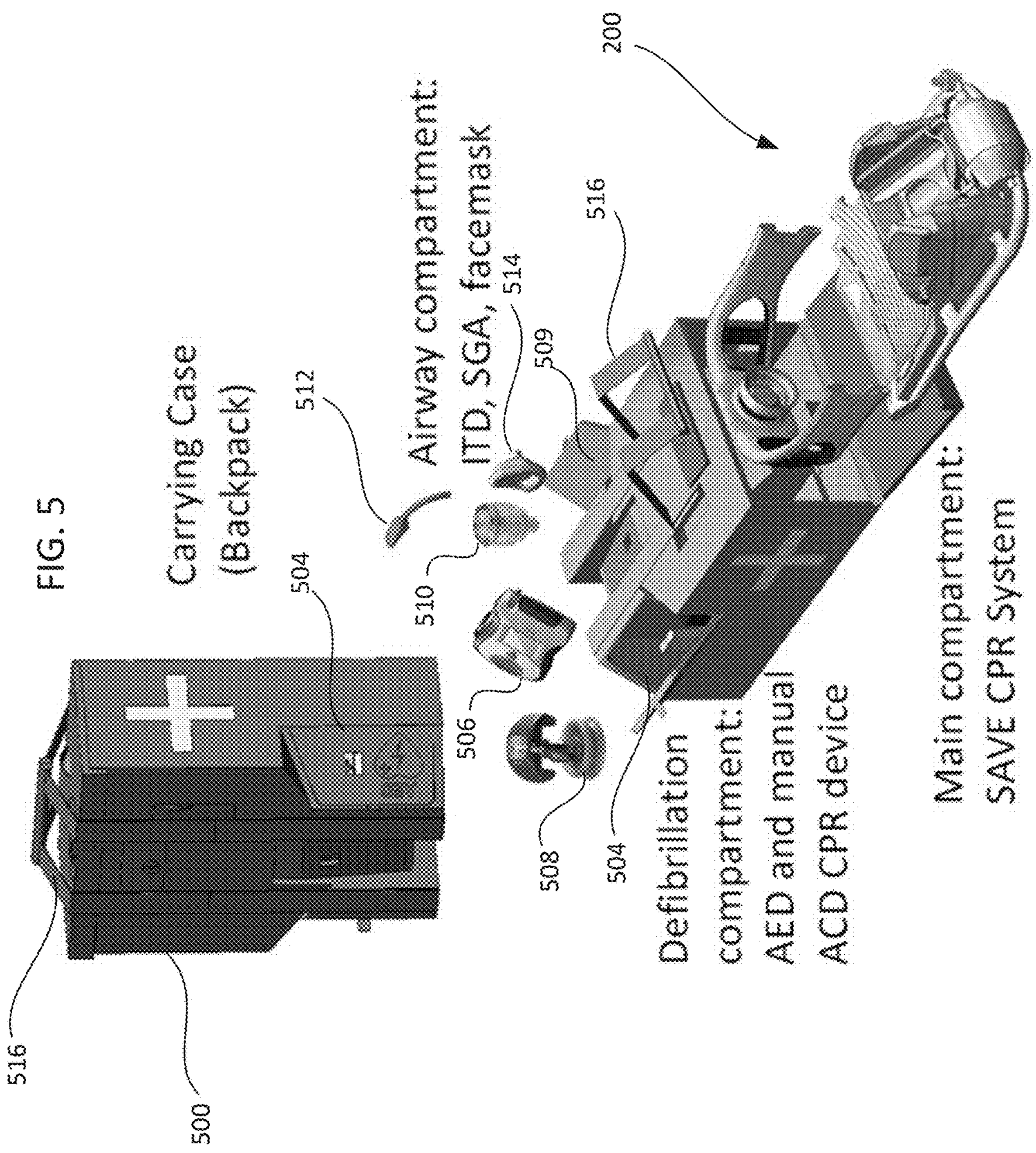
FIG. 5 depicts a carrying case for a head up CPR system according to embodiments.

FIG. 5 illustrates a carrying case 500 that may be used to store and transport the HUP CPR system 100, 200 and/or 400. The carrying case 500 designed to easily fit into first responder vehicles and is easily deployed. For example, the carrying case 500 may include one or more compartments that may hold various resuscitation equipment. In some embodiment, a main compartment 502, may be used to store the HUP CPR system, including the chest compression device. One or more additional compartments may be included in carrying case 500. For example, a defibrillation compartment 504 may include an automated external defibrillator (AED) 506 and/or a manual CPR device 508, such as a manual ACD CPR device. The AED 506 include electrode pads that may be applied to the bare chest of the patient. In some embodiments, an AED 506 may be configured to autonomously analyze a patient's condition. In such embodiments, when operated, the electrode pads may allow the AED 506 to examine the electrical output from the heart and determine if the patient is in a shockable rhythm (either ventricular fibrillation or ventricular tachycardia). If the device determines that a shock is warranted, the AED 506 will use a battery to charge an internal capacitor and, when charged, delivers a shock to the patient's chest. In non-autonomous modes, an operator of the AED 506 may interact with the AED 506 (such as by interacting with a user interface of the AED) to trigger the delivery of a shock. In some embodiments, after the first shock is delivered the AED 506 may analyze the patient and either instruct CPR to be performed, or prepare to administer another shock. In some embodiments, the strength, duration, and/or sequence of shocks may be adjusted, either manually or automatically based on the sensed heart rhythm of the patient. The shocks from an AED 506 are typically between about 100-400 joules, with ranges of about 120-200 joules being more common. For example, newer AEDs often use biphasic algorithms that administer two sequential lower-energy shocks of 120-200 joules, with each shock moving in an opposite polarity between the pads. This lower-energy waveform may be more effective based on some clinical tests, as well as offering a reduced rate of complications and reduced recovery time. In some embodiments, the AED 506 may provide audio and/or visual feedback to a rescuer regarding a quality of chest compressions being administered.

The carrying case 500 may include an airway compartment 509 that may house an ITD 510, a supraglottic airway (SGA) device 512, a facemask 514, additional manual ventilation bags, and/or other ventilation or airway management equipment. It will be appreciated that the number and/or layout of compartments may vary based on the needs of a particular application and that the above description of compartments and associated equipment is merely one example, and that numerous configurations exist. Moreover, equipment may be arranged in the various compartments in any manner. In some embodiments, the carrying case 500 may include one or more handles or straps 516 that may be used to carry and transport the carrying case 500. For example, the carrying case 500 may include two shoulder straps 516 that may enable the carrying case 500 to be carried as a backpack.

Example 1

Figure 6:
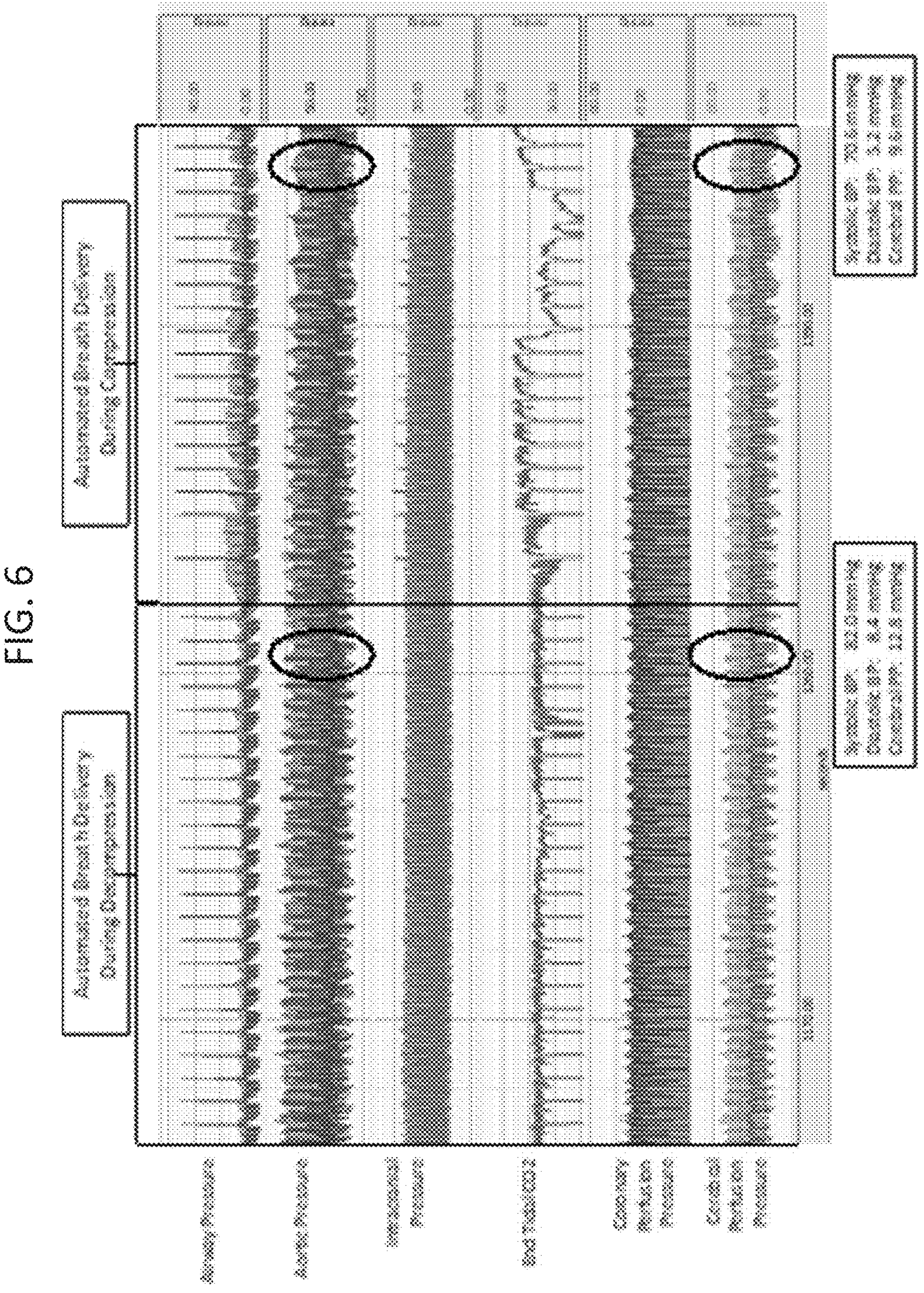
FIG. 6 is a graph showing pressure tracings during the performance of CPR with synchronized ventilations.

A pig study was performed to demonstrate the feasibility of and physiology associated with using a mechanical resuscitator bag squeezer, similar to what is illustrated in FIGS. 4A-4C, and a sensor to trigger the automated breath delivery in a repeatable, synchronized manner during the CPR cycle. FIG. 6 shows a series of pressure tracings from that study. The anesthetized pig was put into cardiac arrest and CPR was perform with a HUP CPR device as shown in FIG. 1. Active compression decompression CPR was performed at 100 down-up cycles/min and an impedance threshold device (ITD-16) was attached to the endotracheal tube to regulate intrathoracic pressures. A sensor was attached to the backplate of the compression device (FIG. 1J, component 108) that sensed each time there was a chest compression. As shown in FIG. 6, compression of the prototype resuscitator bag could be timed such that the automated breath delivery could occur during the compression phase (pressure tracings on the left) or during the compression phase (tracings on the right). Each automated breath delivery is about 200 ms and in this 40 kg pig about 400 ml on the left when the breath was delivered during the decompression phase. Upon switching the delivery of the breath to synchronize with the compression phase there was an immediate increase in intrathoracic/airway pressure (top tracing) and a decline in aortic pressure and cerebral perfusion pressure. After just 10-12 automated breaths synchronized to the compression phase key hemodynamic variables such as aortic pressure and cerebral perfusion pressure were decreased when breaths were delivered during the compression phase as the excessively high positive pressure peek intrathoracic pressures. As shown, limited venous return to the heart, caused 'air-trapping' or 'auto-PEEP' (positive end expiratory pressure) in the lungs as the air was trapped and could not get out, and reduced the total tidal volume (breath delivered) from 400 ml per breath to 200 ml per breath, as the pressure during compression of the bag simultaneously with compression of the chest blocked half of the positive pressure breath from getting in to the lung. The reduced tidal volume delivered caused a rise in expired $CO_2$ as it was more concentrated in the lower volume of inspired and expired gases. By contrast, delivery of the breath during the chest decompression resulted in superior hemodynamics (higher blood pressure and cerebral perfusion pressure) and end tidal $CO_2$ values that are normal in value. Automated breath delivery synchronized with the decompression phase of CPR is superior to unsynchronized positive pressure ventilation or breaths synchronized to be given just during the CPR compression phase. These findings are generalizable to conventional CPR without head up or ACD+ITD as well.

Figure 7:
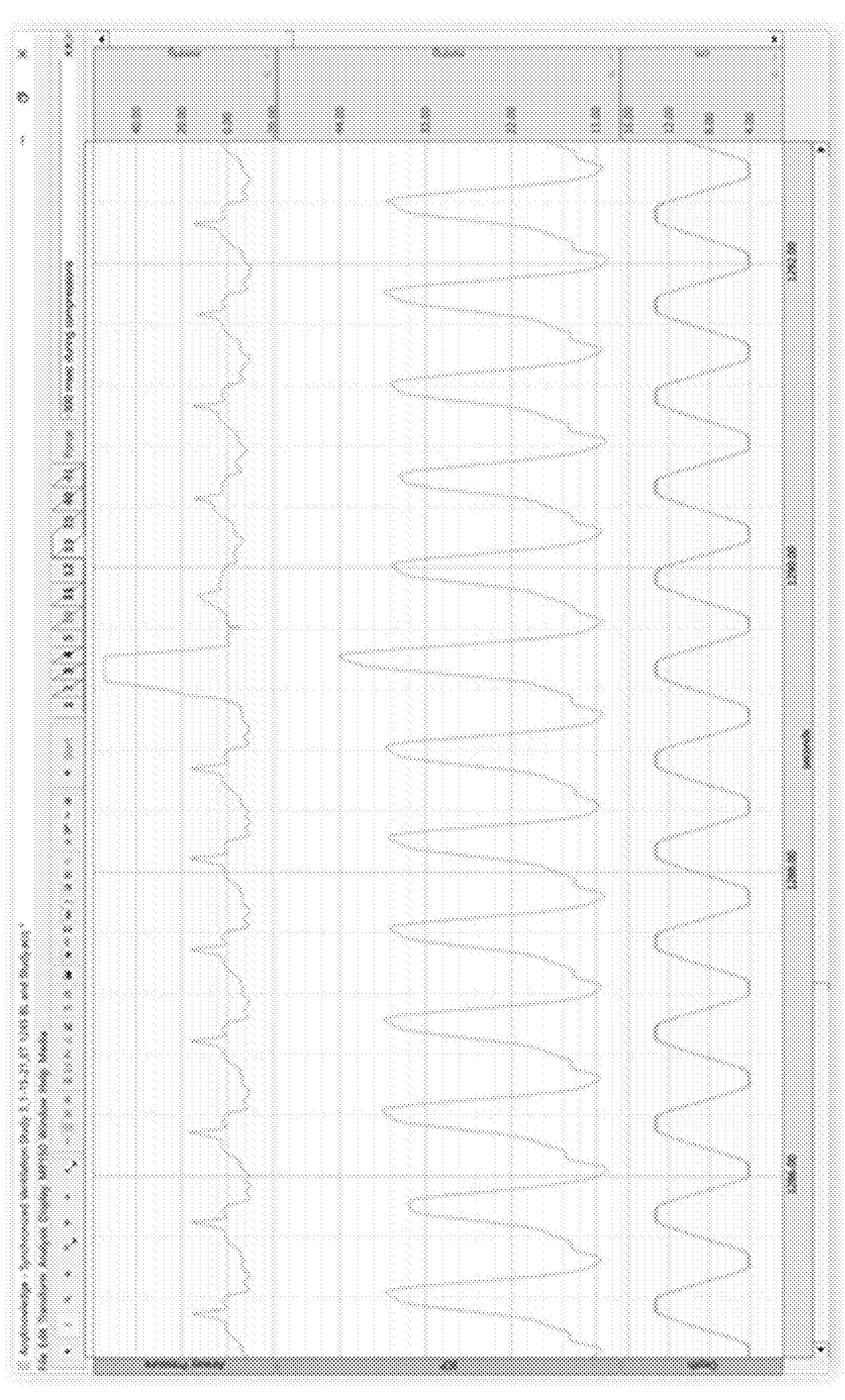
FIG. 7 is a graph showing intracranial pressures during the performance of CPR with positive pressure ventilations synchronized with a compression phase of CPR.
Figure 8:
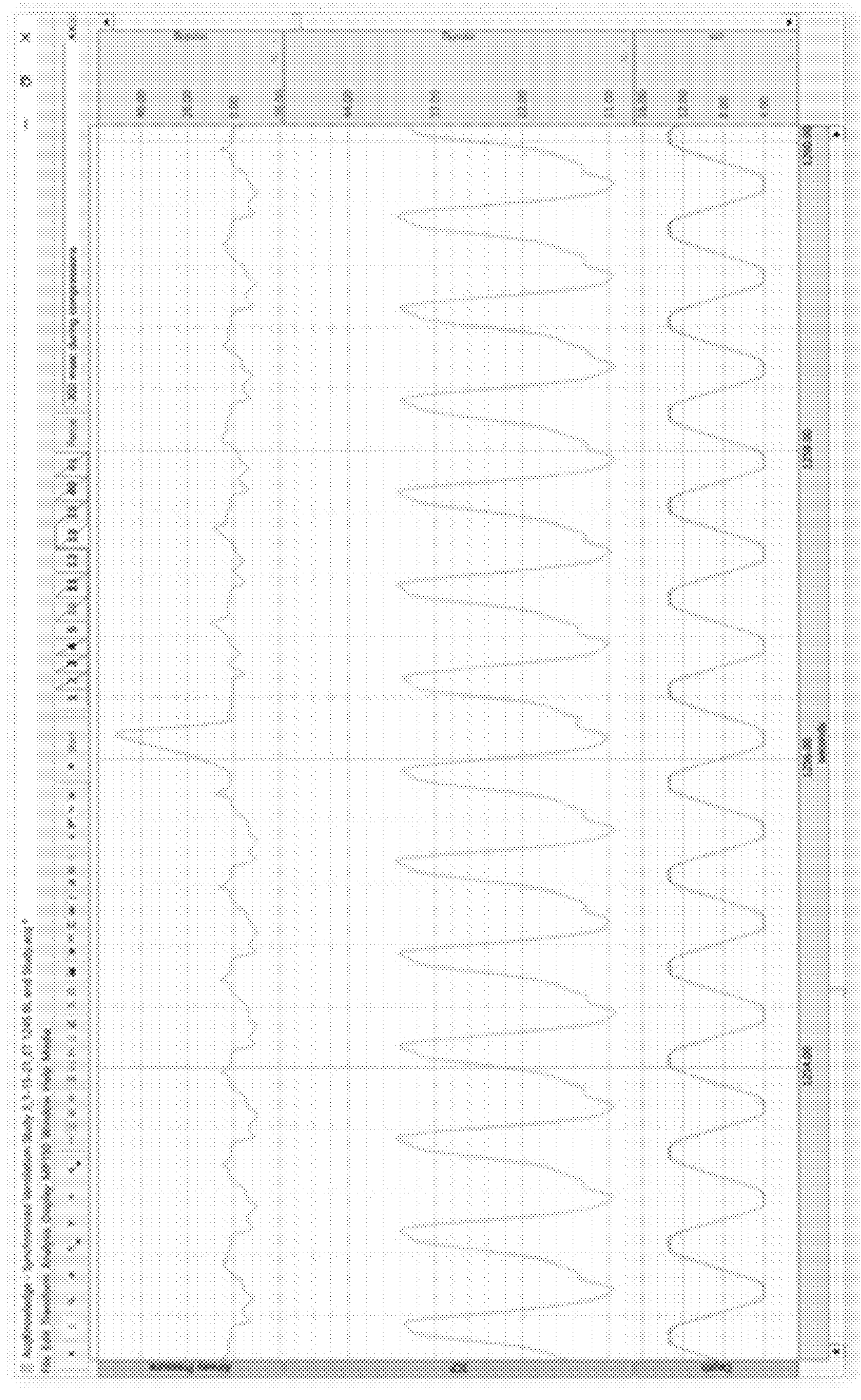
FIG. 8 is a graph showing intracranial pressures during the performance of CPR with positive pressure ventilations synchronized with a decompression phase of CPR.

Additional detail is shown in FIGS. 7 and 8. When a positive pressure breath is delivered during the compression phase, intracranial pressures are elevated even further (this is harmful) and airway pressure exceed 50 mmHg (FIG. 7). By contrast, when the positive pressure breath is synchronized with the decompression phase, as shown in FIG. 8, the ICP values are lower and less dangerous. It should be noted that when rescue personnel provide positive pressure ventilations by manually squeezing a resuscitator bag that multiple errors are common including excessive ventilation rates, too large or too small a tidal volume, and providing the breath too quickly or too slowly. These errors are difficult to avoid in the heat of the moment during the resuscitation effort and there are only a limited number of ways to prevent these errors. The inventions described herein were created in an effort to provide consistent ventilation rate, tidal volume, and speed of breath delivery safely. Moreover, the inventions are designed to minimize increases in the amplitude or duration of intrathoracic pressure during CPR. While a rise in intrathoracic pressure is needed to inflate the lungs and deliver a positive pressure ventilation, there is a balance between these beneficial effects and the harmful effects of excessively high or prolonged intrathoracic pressure. If the intrathoracic pressure is too high or too prolonged, it reduces venous blood flow back to the heart and increases intracranial pressure: these combined effects markedly limit blood flow to the brain. (see Aufderheide, T. P. & Lurie, K. G. Death by hyperventilation: a common and life-threatening problem during cardiopulmonary resuscitation. *Critical care medicine* 32, S345-351 (2004).)

Example 2

The methods and devices described in this application can be used to increase neurologically intact survival after cardiac arrest in a fully automated CPR system that includes a device to elevate the head and thorax in a controlled and sequential manner (e.g. an automated head up CPR positioning device or AHUP), a compression-decompression (ACD) device that compresses the chest between 16-25% of the anterior-posterior diameter, and/or nominally 1.8 to 2.4 inches using a suction cup or other means to actively decompress the chest, a means to regulate intrathoracic pressure such as an impedance threshold device (ITD) or and/or inspiratory resistor valve as described in U.S. Pat. Nos. 5,551,420; 5,692,498; 5,730,122; 6,029,667; 6,062,219; 6,155,257; 6,234,916; 6,224,562; 6,526,973; 6,604,523; 6,986,349; 7,204,251; and 11,103,672 (the complete disclosures of which are herein incorporated by reference), and an automated breath delivery (ABD) device that provides controlled positive pressure ventilations to the patient. The synergistic effects of ACD+ITD+AHUP have never been observed before in humans to be associated with increased survival to hospital discharge with favorable neurological function. The novel clinical benefits of ACD+ITD+AHUP are described herein.

Survival after out-of-hospital cardiac arrest (OHCA) remains poor worldwide. A physiologically-distinct neuroprotective (NP) cardiopulmonary resuscitation (CPR) strategy that combined automated head-up positioning (AHUP), an impedance threshold device (ITD), and manual active compression-decompression (ACD) and/or an automated suction-cup based compression device was recently shown in animal models to increase cerebral blood flow and neurologically-intact survival. The effectiveness of NP-CPR on survival to hospital discharge was assessed in patients after OHCA.

This was an observational study from a prospective registry of adult out-of-hospital cardiac arrest (OHCA) patients treated with NP-CPR (n=227) from 04/2019 to 07/2020 from 6 pre-hospital systems located throughout the United States. Individual conventional (C) CPR control subject data (n=5,352) were obtained from three large published OHCA randomized controlled trials from high-performing pre-hospital systems. The primary study outcome was survival to hospital discharge. Secondary outcomes included hospital survival with favorable neurological function. Multivariable logistic regression and propensity-score 4:1 (C-CPR:NP-CPR) matching analyses were performed to account for imbalances in baseline characteristics.

Despite less favorable baseline clinical characteristics in the NP-CPR group, faster initiation of NP-CPR was associated with higher adjusted odds ratios (ORs) of survival to hospital discharge and favorable neurological survival, using multivariable and propensity score matching analyses. After propensity-score matching, the ORs of survival to hospital discharge for NP-CPR relative to C-CPR were 4.02 (95% confidence interval [CI], 1.68 to 9.62) and 2.01 (95% CI, 1.07 to 3.79) when NP-CPR was initiated within 10 and 15 minutes after the emergency call for help, respectively. The corresponding ORs of favorable neurological survival were 3.43 (95% CI, 1.21 to 9.71) and 1.91 (95% CI, 0.91 to 4.03), respectively.

Compared with matched C-CPR controls, rapid NP-CPR application was associated with a significantly higher probability of survival to hospital discharge after OHCA.

Data used in the study were obtained from 409 patients treated with NP-CPR and entered in the registry between April 2019 and July 2020. A total of 6 of the 10 EMS systems that participated in the registry contributed 227 patients that met study inclusion criteria. The 6 EMS systems were 1) Edina, Minnesota; 2) Anoka County, Minnesota; 3) Germantown, Tennessee; 4) Little Rock, Arkansas; 5) Palm Beach County, Florida; and 6) Miami, Florida. For the control (C-CPR) group, corresponding individual participant data were available for 1,192, 2,825, and 1,335 individuals from the ROC-PRIMED Study, ROC-ALPS, and ResQTrial studies, respectively. Overall, the analytical sample consisted of 227 NP-CPR and 5,352 C-CPR patients.

Each NP-CPR recipient could be matched to four C-CPR individuals, resulting in a propensity score matched sample size of 1,135 individuals. After propensity score matching, adequate overlap in propensity score was observed and no residual imbalance in baseline characteristics persisted between NP-CPR and C-CPR recipients, with the exception that the median time elapsed from 9-1-$1_{TIME}$ to EMS CPR was 1 minute longer in the NP-CPR group. Nonetheless, rapid initiation of NP-CPR was associated with significantly higher OR for survival to hospital discharge versus C-CPR as shown in FIG. 9, which illustrates a comparison of survival to hospital discharge between conventional (C) and neuroprotective (NP) CPR according to time interval from the 9-1-1-emergency call for help to Automated Head Up Position device placement after propensity-score matching. The propensity score was derived from a non-parsimonious multivariable logistic regression model that predicted the receipt of neuroprotective CPR, with age, sex, EMS-witnessed arrest, bystander-witnessed arrest, bystander CPR attempt, shockable rhythm, and elapsed time from emergency call to EMS CPR entered as covariates. The time from emergency 9-1-1 call to Automated Head Up Position device placement was a surrogate for the 9-1-1 call to NP-CPR start interval. The OR of survival to hospital discharge was 5.10 (95% CI 1.72-15.09) when the 9-1-$1_{TIME}$ to NP-CPR start interval was <8 minutes and remained significantly higher than 1.00 when 9-1-$1_{TIME}$ to NP-CPR start interval within 15 minutes. There was a decrease in the survival OR for NP-CPR relative to C-CPR recipients with each minute delay in the NP-CPR start interval over this time frame. The OR of survival to hospital discharge with favorable neurological function with NP-CPR relative to C-CPR was 5.08 (95% CI 1.28-20.08) when the 9-1-$1_{TIME}$ to NP-CPR start time interval was within 7 minutes and remained significantly higher than 1.00 when the 9-1-$1_{TIME}$ to NP-CPR start interval was <13 minutes as shown in FIG. 10, which illustrates a comparison of survival to hospital discharge with favorable neurological outcome between conventional (C) and neuroprotective (NP) CPR according to time interval from the 9-1-1-emergency call for help to Automated Head Up Position device placement after propensity-score matching. The propensity score was derived from a non-parsimonious multivariable logistic regression model that predicted the receipt of neuroprotective CPR, with age, sex, EMS-witnessed arrest, bystander-witnessed arrest, bystander CPR attempt, shockable rhythm, and elapsed time from emergency call to EMS CPR entered as covariates. The time from emergency 9-1-1 call to Automated Head Up Position device placement was a surrogate for the 9-1-1 call to NP-CPR start interval. The value for survival to hospital discharge with favorable neurological outcome was missing for two C-CPR individuals. For the ROSC outcome, the OR was significant was significantly higher than 1.00 when NP-CPR was started within 9 to 12 minutes of the 9-1-$1_{TIME}$ in comparison with matched C-CPR controls.

Results from this prospective registry-based study found that rapid application of NP-CPR was associated with a higher likelihood of survival to hospital discharge following OHCA compared with C-CPR. These findings represent the first clinical evidence that rapid NP-CPR implementation after OHCA is closely associated with an increased likelihood of survival to hospital discharge. Both multivariable logistic regression and propensity score matching analyses were performed with similar findings for the primary and secondary study endpoints. With adjustment for important confounders, we observed a time-dependent beneficial association of NP-CPR versus C-CPR controls from high-performing North American pre-hospital systems. The sooner NP-CPR could be implemented, the better the outcome. Rapid deployment of NP-CPR was also associated with significantly improved ROSC rates and neurologically favorable survival when compared with C-CPR controls.

The current results reflect an advanced CPR systems approach with multiple resuscitation interventions working together. Each individual NP-CPR element utilizes different but complementary mechanisms to improve pre-load, preserve mean arterial pressure, reduce ICP, enhance venous drainage from the brain, and improve cardio-cerebral blood flow. They have been shown in previous translational studies to be inter-dependent, time dependent, and synergistic when combined together with proper sequencing. Moreover, as cardiac arrest is a complex and heterogenous disease state, the association of NP-CPR with improved outcomes is also dependent on effective implementation of many elements of the chain of survival that precede initiation of CPR and follow ROSC.

These findings represent is a major advance in resuscitation and it can be uniquely performed in a fully automated manner with the inventions described in this application, including automated breath delivery systems as described herein.

Specific details are given in the description to provide a thorough understanding of example configurations (including implementations). However, configurations may be practiced without these specific details. For example, well-known processes, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure. Additionally, features described in relation to one embodiment may be incorporated into other embodiments while staying within the scope of the disclosure.

Also, configurations may be described as a process that is depicted as a flow diagram or block diagram. Although each may describe the operations as a sequential process, many of the operations may be performed in parallel or concurrently. In addition, the order of the operations may be rearranged. A process may have additional steps not included in the figure.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A head up CPR system, comprising:

a base;

an upper support coupled with the base and configured to elevate a patient's upper body;

a chest compression device that is couplable with one or both of the base and the upper support; and a positive pressure ventilation system that is structurally mountable to the base, wherein:

the positive pressure ventilation system comprises a resuscitator bag and an automated resuscitator bag compressor; and the resuscitator bag is removable from the automated resuscitator bag compressor for operation in a manual mode.

2. The head up CPR system of claim 1, wherein:

the positive pressure ventilation system comprises:

the manual resuscitator bag;

a mechanical linkage system; and an actuator that drives the mechanical linkage system.

3. The head up CPR system of claim 1, further comprising:

an impedance threshold device that is configured to be interfaced with the positive pressure ventilation system.

4. The head up CPR system of claim 1, further comprising:

an automated external defibrillator.

5. The head up CPR system of claim 1, wherein:

the chest compression device is further configured to actively decompress an individual's chest between each compression.

6. The head up CPR system of claim 1, wherein:

the positive pressure ventilation system is configured to receive a signal that synchronizes delivery of a positive pressure ventilation with one or more phases of CPR compression/decompression cycles with one or both of continuous uninterrupted chest compressions and interrupted chest compressions.

7. The head up CPR system of claim 6, wherein:

the positive pressure ventilation system is controlled by one or both of an on/off switch and a signal that synchronizes delivery of a positive pressure ventilation with a phase of CPR.

8. The head up CPR system of claim 6, wherein:

the signal is received from one or both of a sensor and a controller.

9. The head up CPR system of claim 1, wherein:

the positive pressure ventilation system is configured to deliver positive pressure ventilations that have durations of between about 300 msec and 1200 msec.

10. The head up CPR system of claim 1, wherein:

the positive pressure ventilation system, the upper support, and the chest compression device are controlled by a same controller system.

11. The head up CPR system of claim 1, wherein:

the upper support is configured to elevate the patient's upper body from a starting position to an elevated position over a period of between about 30 seconds and 4 minutes.

12. The head up CPR system of claim 1, further comprising:

a controller that is configured to adjust one or more of a ventilation rate, a tidal volume, and a compression: ventilation ratio.

13. The head up CPR system of claim 1, wherein:

the positive pressure ventilation system is configured to receive a selection for one or more parameters selected from the group consisting of a positive pressure ventilation delivery rate, a tidal volume, and a duration of positive pressure ventilation delivery.

14. The head up CPR system of claim 1, further comprising:

a carrying case comprising one or more compartments that are configured to hold the base and the upper support, the chest compression device, and the positive pressure ventilation system.

15. A method of increasing the probability of survival with good brain function in a sudden cardiac arrest patient, comprising:

positioning a patient on a head up CPR system such that a chest compression device of the head up CPR system is aligned with the patient's heart;

elevating a portion of the patient's upper body;

performing chest compressions and active chest decompression on the patient using a chest compression device of the head up CPR system while the portion of the patient's upper body is elevated; and delivering positive pressure ventilations using a positive pressure ventilation device of the head up CPR system, wherein:

the positive pressure ventilation device is structurally mounted to a base of the head up CPR system;

the positive pressure ventilation system comprises a resuscitator bag and an automated resuscitator bag compressor; and the resuscitator bag is removable from the automated resuscitator bag compressor for operation in a manual mode.

16. The method of increasing the probability of survival with good brain function in a sudden cardiac arrest patient of claim 15, wherein:

delivery of the positive pressure ventilations is synchronized with a phase of CPR.

17. The method of increasing the probability of survival with good brain function in a sudden cardiac arrest patient of claim 15, further comprising:

regulating an intrathoracic pressure of the patient while the portion of the patient's upper body is elevated.

18. The method of increasing the probability of survival with good brain function in a sudden cardiac arrest patient of claim 15, wherein:

elevating a portion of the patient's upper body comprises elevating the patient's head from a first height of between about 8-10 cm to a second height of between about 15-25 cm.

19. The method of increasing the probability of survival with good brain function in a sudden cardiac arrest patient of claim 15, wherein:

a chest compression rate is slowed from around 90-120 compressions/min to 50-80 compressions per minute to allow for more time during the decompression phase when a positive pressure breath is delivered and synchronized with the decompression phase of the CPR cycle.

* * * * *